United States Patent
Choi et al.

(10) Patent No.: US 11,987,561 B2
(45) Date of Patent: May 21, 2024

(54) RESIST UNDERLAYER COMPOSITION, AND METHOD OF FORMING PATTERNS USING THE COMPOSITION

(71) Applicant: Samsung SDI Co., Ltd., Yongin-si (KR)

(72) Inventors: Yoojeong Choi, Suwon-si (KR); Soonhyung Kwon, Suwon-si (KR); Hyeon Park, Suwon-si (KR); Jaeyeol Baek, Suwon-si (KR); Minsoo Kim, Suwon-si (KR); Shinhyo Bae, Suwon-si (KR); Daeseok Song, Suwon-si (KR); Dowon Ahn, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 180 days.

(21) Appl. No.: 17/147,308

(22) Filed: Jan. 12, 2021

(65) Prior Publication Data

US 2021/0230127 A1    Jul. 29, 2021

(30) Foreign Application Priority Data

Jan. 17, 2020 (KR) .................. 10-2020-0006770

(51) Int. Cl.
*C07D 251/34*    (2006.01)
*G03F 7/004*    (2006.01)
(Continued)

(52) U.S. Cl.
CPC ......... *C07D 251/34* (2013.01); *G03F 7/0045* (2013.01); *G03F 7/11* (2013.01); *G03F 7/168* (2013.01); *G03F 7/26* (2013.01)

(58) Field of Classification Search
CPC .......... G03F 7/0045; G03F 7/11; G03F 7/168; G03F 7/26; G03F 7/091; G03F 7/094;
(Continued)

(56) References Cited

U.S. PATENT DOCUMENTS

| 6,022,500 A  * | 2/2000 | John ...................... B01J 13/18 |
| | | 264/4.1 |
| 2004/0253535 A1* | 12/2004 | Cameron ............... G03F 7/094 |
| | | 430/271.1 |

(Continued)

FOREIGN PATENT DOCUMENTS

| CN | 105093833 A | 11/2015 |
| CN | 108388079 A | 8/2018 |

(Continued)

OTHER PUBLICATIONS

Taylor Ware, Abby R. Jennings, Zahra S. Bassampour, Dustin Simon, David Y. Son and Walter Voit, "Degradable, silyl ether thiol-ene networks", RSC Adv., 2014,4, 39991 (Year: 2014).*

(Continued)

*Primary Examiner* — Sean M DeGuire
*Assistant Examiner* — Alexander Nicholas Lee
(74) *Attorney, Agent, or Firm* — Lewis Roca Rothgerber Christie LLP

(57) ABSTRACT

A resist underlayer composition includes (A) a polymer including a structural unit represented by Chemical Formula 1, a compound represented by Chemical Formula 2, or a combination thereof; (B) a polymer including a structure in which at least one moiety represented by Chemical Formula 3 or Chemical Formula 4 and a moiety represented by (Continued)

Chemical Formula 7 are bound to each other; and (C) a solvent:

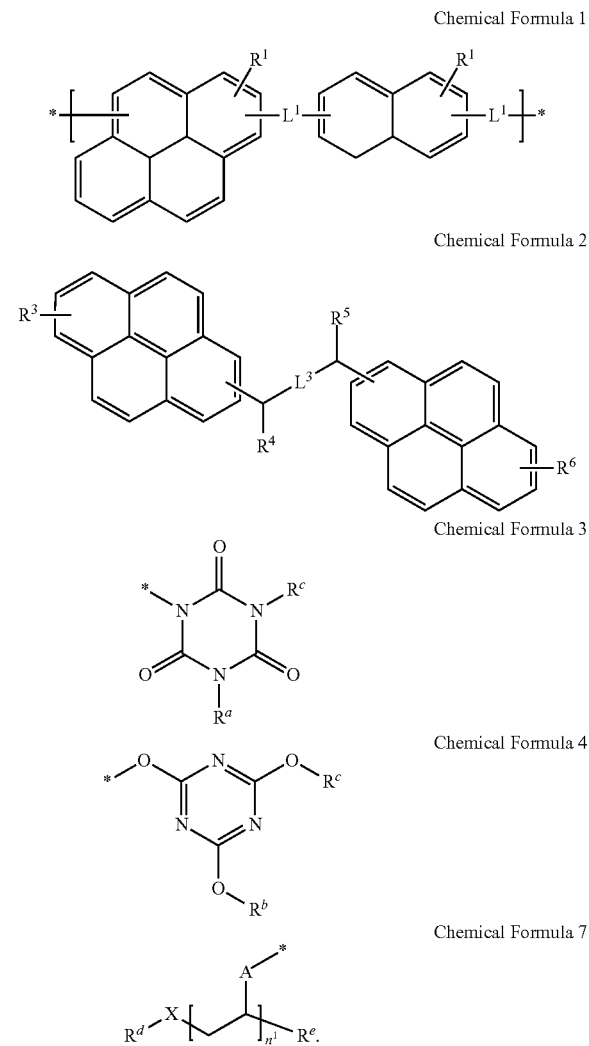

Chemical Formula 1

Chemical Formula 2

Chemical Formula 3

Chemical Formula 4

Chemical Formula 7

17 Claims, 2 Drawing Sheets

(51) Int. Cl.
| | |
|---|---|
| *G03F 7/11* | (2006.01) |
| *G03F 7/16* | (2006.01) |
| *G03F 7/26* | (2006.01) |

(58) Field of Classification Search
CPC ... G03F 7/004; G03F 7/09; G03F 7/20; G03F 7/2041; C07D 251/34; C08L 65/00; C08L 101/00
See application file for complete search history.

(56) References Cited

U.S. PATENT DOCUMENTS

| | | | |
|---|---|---|---|
| 2008/0305441 | A1 | 12/2008 | Yoon et al. |
| 2015/0274622 | A1* | 10/2015 | Kim ........................ C07C 39/14 216/49 |
| 2015/0329718 | A1* | 11/2015 | Choi ................... H01L 21/0332 524/611 |
| 2017/0007505 | A1 | 1/2017 | Moszner et al. |
| 2018/0224744 | A1* | 8/2018 | Bae ..................... H01L 21/3081 |
| 2019/0196332 | A1 | 6/2019 | Park |

FOREIGN PATENT DOCUMENTS

| | | |
|---|---|---|
| CN | 110041345 A | 7/2019 |
| JP | 6083537 B2 | 2/2017 |
| KR | 10-2013-0078745 A | 7/2013 |
| KR | 10-2013-0079150 A | 7/2013 |
| KR | 10-2014-0050046 A | 4/2014 |
| KR | 10-2014-0085123 A | 7/2014 |
| KR | 10-2015-0002928 A | 1/2015 |
| KR | 10-2016-0060035 A | 5/2016 |
| KR | 10-2016-0060263 A | 5/2016 |
| KR | 10-2016-0126353 A | 11/2016 |
| KR | 10-2016-0146691 A | 12/2016 |
| KR | 10-2017-0070017 A | 6/2017 |
| KR | 10-2017-0087295 A | 7/2017 |
| KR | 10-2018-0090640 A | 8/2018 |
| KR | 10-2019-0011478 A | 2/2019 |
| KR | 10-2019-0078304 A | 7/2019 |
| KR | 10-2019-0125765 A | 11/2019 |
| TW | 202000742 A | 1/2020 |
| WO | WO 2005/088398 A1 | 9/2005 |
| WO | 2010061774 A1 | 6/2010 |
| WO | WO 2013/141015 A1 | 9/2013 |
| WO | 2016-208300 A1 | 12/2016 |
| WO | 2016-208518 A1 | 12/2016 |
| WO | WO 2017/126780 A1 | 7/2017 |
| WO | 2017-141612 A1 | 8/2017 |

OTHER PUBLICATIONS

"Further Discussion on . . . Polymerization Behavior of Triallyl Isocyanurate", Akira Matsumoto, Shunsuke Ogawa, Tomoya Matsuda, Akihiro Ueda, Hiroyuki Aota, Toshifumi Fujii, and Hiroyuki Toridome. Macromolecules 2008, 41 (21), 7938-7945 (Year: 2008).*
Ware, Taylor et al., "Degradable, silyl ether thiol-ene networks," *RSC Advances* (2014), vol. 4 pp. 39991-40002.
Notice of Allowance dated Jan. 18, 2022 of the corresponding Japanese Patent Application No. 2021-004158 (3 pages).
Taiwanese Office Action dated Aug. 31, 2021 issued in corresponding Taiwanese Patent Application No. 110101582, 4 pages.
Chinese Office action dated Mar. 27, 2024, corresponding to Chinese Patent Application No. 202110056902.7, 5 pages.

* cited by examiner

RESIST UNDERLAYER COMPOSITION, AND METHOD OF FORMING PATTERNS USING THE COMPOSITION

CROSS-REFERENCE TO RELATED APPLICATION

This application claims priority to and the benefit of Korean Patent Application No. 10-2020-0006770, filed in the Korean Intellectual Property Office on Jan. 17, 2020, the entire content of which is incorporated herein by reference.

BACKGROUND

1. Field

One or more aspects of embodiments of the present disclosure relate to a resist underlayer composition, and a method of forming a pattern using the same.

2. Description of the Related Art

Recently, the semiconductor industry has developed to an ultrafine technique (e.g., level of technology) having a pattern size of scale of several to several tens of nanometers. Effective lithographic techniques are desired for production of such semiconductor devices.

A lithographic technique is a processing method that includes coating a photoresist layer on a semiconductor substrate (such as a silicon wafer) to form a thin film, irradiating the photoresist layer with activating radiation (such as ultraviolet rays) through a mask pattern on which the device pattern is drawn, developing the resultant to obtain a photoresist pattern, and etching the substrate using the photoresist pattern as a protective layer to form a fine pattern, corresponding to the mask pattern, on the surface of the substrate.

The quality of the exposure performed during formation of the photoresist pattern is among the important factors for obtaining a photoresist image with a high resolution.

As ultrafine pattern manufacturing technology is required, light sources that can produce short wavelengths (such as i-line (a wavelength of 365 nm), KrF excimer laser (a wavelength of 248 nm), and/or ArF excimer laser (a wavelength of 193 nm)) are used as activated radiation sources for exposure of photoresists. Accordingly, in order to solve problems caused by diffuse reflection or standing waves of the activated radiation on the semiconductor substrate, a resist underlayer having a desired or optimized reflectance has been introduced between the resist and the semiconductor substrate.

As an alternative to the activated radiation, a method of using high energy rays (such as EUV (extreme ultraviolet; a wavelength of 13.5 nm), E-Beam (electron beam), and/or the like) as a light source for forming a fine pattern is also performed. The high energy light source has almost or substantially no reflection from a substrate, but as the pattern is refined, a thinner resist underlayer is desired, and in order to improve collapse of the formed pattern, research on improving the adhesion between the resist and the underlayer is being conducted. In order to maximize or increase efficiency of the light source, research on sensitivity through the underlayer is also being conducted.

SUMMARY

One or more aspects of embodiments of the present disclosure are directed toward a resist underlayer composition that is capable of improving patterning performance and efficiency by improving sensitivity (e.g., the sensitivity of a resist) to an exposure light source, does not cause a pattern collapse of the resist even in a fine patterning process, and is formed into a thin film so that an etching process time may be shortened.

One or more aspects of embodiments of the present disclosure are directed toward a method of forming patterns using the resist underlayer composition.

One or more example embodiments of the present disclosure provide a resist underlayer composition including:

(A) a polymer including a structural unit represented by Chemical Formula 1, a compound represented by Chemical Formula 2, or a combination thereof;

(B) a polymer including a structure in which at least one moiety represented by Chemical Formula 3 or Chemical Formula 4, and a moiety represented by Chemical Formula 7 are bound to each other; and (C) a solvent:

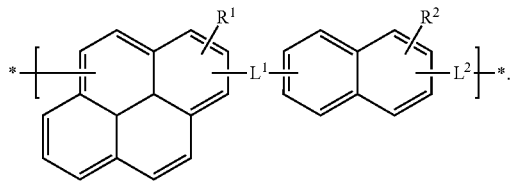

Chemical Formula 1

In Chemical Formula 1, $R^1$ and $R^2$ are each independently a hydroxy group, a substituted or unsubstituted C1 to C20 alkoxy group, a halogen, a substituted or unsubstituted C1 to C20 alkyl group, a substituted or unsubstituted C2 to C30 alkenyl group, a substituted or unsubstituted C2 to C20 alkynyl group, a substituted or unsubstituted C6 to C30 aryl group, a substituted or unsubstituted C6 to C30 heteroaryl group, a substituted or unsubstituted vinyl group, or a combination thereof, $L^1$ and $L^2$ are each independently a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, and is a linking point;

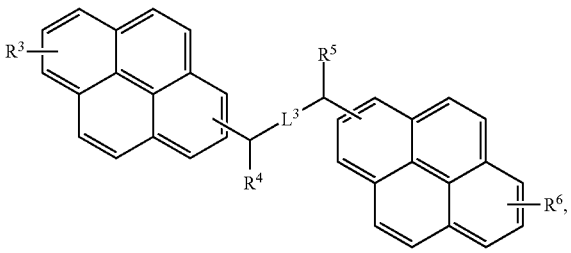

Chemical Formula 2 wherein, in Chemical Formula 2, $R^3$ to $R^6$ are each independently a hydroxy group, a thiol group, a cyano group, a substituted or unsubstituted amino group, a halogen atom, a substituted or unsubstituted C1 to C30 alkyl group, a substituted or unsubstituted C1 to C30 alkoxy group, a substituted or unsubstituted C6 to C30 aryl group, or a combination thereof, and $L^3$ is a single bond, a substituted or unsubstituted C1 to C30 alkylene group, a substituted or unsubstituted C6 to C30 arylene group, or a combination thereof;

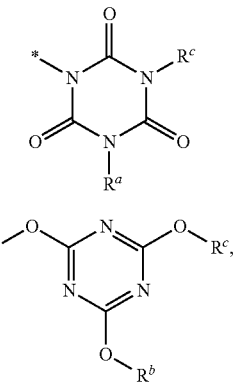

Chemical Formula 3

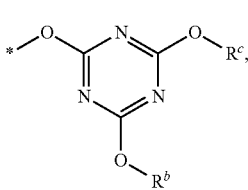

Chemical Formula 4 wherein, in Chemical Formulae 3 and 4, $R^a$ and $R^b$ are each independently hydrogen, deuterium, a substituted or unsubstituted C1 to C10 alkyl group, a substituted or unsubstituted C2 to C20 alkenyl group, a substituted or unsubstituted C2 to C20 vinyl group, a substituted or unsubstituted C2 to C20 alkynyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C2 to C20 heteroalkenyl group, a substituted or unsubstituted C3 to C20 heterocycloalkyl group, or a substituted or unsubstituted C6 to C20 heteroaryl group, or a combination thereof, $R^c$ is a terminal group that is a substituted or unsubstituted C1 to C10 alkyl group, a substituted or unsubstituted C2 to C20 alkenyl group, a substituted or unsubstituted C2 to C20 alkynyl group, a substituted or unsubstituted C3 to C20 cycloalkyl group, a substituted or unsubstituted C1 to C10 heteroalkyl group, a substituted or unsubstituted C2 to C20 heteroalkenyl group, a substituted or unsubstituted C3 to C20 heterocycloalkyl group, a structural unit represented by Chemical Formula 5 or Chemical Formula 6, or a combination thereof, and the at least one moiety represented by Chemical Formula 3 or 4 is linked to * in Chemical Formula 7 at each * position;

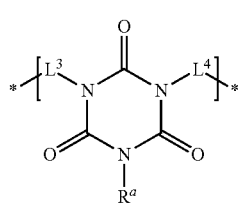

Chemical Formula 5

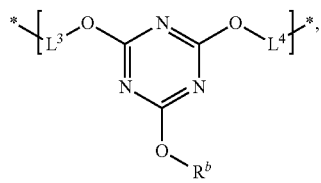

Chemical Formula 6 wherein, in Chemical Formulae 5 and 6, $L^3$ and $L^4$ are each independently a substituted or unsubstituted C1 to C20 alkylene group, a substituted or unsubstituted C1 to C20 heteroalkylene group, or a combination thereof, $R^a$ and $R^b$ are each independently the same as defined in Chemical Formula 3 and Chemical Formula 4, and
is a linking point; and

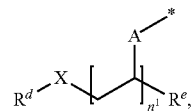

Chemical Formula 7 wherein, in Chemical Formula 7,

A is a single bond, a substituted or unsubstituted C1 to C10 alkylene group, —C(=O)—, —(CO)O—, —O(CO)O—, or a combination thereof, X is a single bond, —O—, —S—, —S(=O)—, —S(=O)$_2$—, —C(=O)—, —(CO)O—, —O(CO)O—, —NR— (wherein R is hydrogen, deuterium, or a C1 to C10 alkyl group), or a combination thereof, $R^d$ is hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, $R^e$ is one of hydrogen, deuterium, or a C1 to C10 alkyl group, $n^1$ is 1 to 10,000, and is linked to Chemical Formula 3 or Chemical Formula 4, or linked to hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, provided that at least one of Chemical Formula 3 or Chemical Formula 4 is linked to * of Chemical Formula 7.

In some embodiments, $R^1$ and $R^2$ of Chemical Formula 1 may each independently be a hydroxy group, a substituted or unsubstituted C1 to C20 alkoxy group, a substituted or unsubstituted C1 to C20 alkyl group, a substituted or unsubstituted C6 to C30 aryl group, a substituted or unsubstituted vinyl group, or a combination thereof, $L^1$ and $L^2$ of Chemical Formula 1 may each independently be a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, $R^3$ to $R^6$ of Chemical Formula 2 may each independently be a hydroxy group, a thiol group, a cyano group, a substituted or unsubstituted C1 to C30 alkoxy group, or a combination thereof, and $L^3$ of Chemical Formula 2 may be a substituted or unsubstituted phenylene group, a substituted or unsubstituted naphthalenylene group, a substituted or unsubstituted biphenylene group, or a combination thereof.

In some embodiments, $R^a$ and $R^b$ of Chemical Formulae 3 and 4 may each independently be a substituted or unsubstituted C1 to C10 alkyl group, a substituted or unsubstituted C2 to C20 alkenyl group, a substituted or unsubstituted C3 to C20 cycloalkyl group, a substituted or unsubstituted C1 to C10 heteroalkyl group, a substituted or unsubstituted C2 to C20 heteroalkenyl group, or a substituted or unsubstituted C3 to C20 heterocycloalkyl group, $R^c$ may be a terminal group that is a substituted or unsubstituted C1 to C10 alkyl group, a substituted or unsubstituted C3 to C20 cycloalkyl group, a substituted or unsubstituted C1 to C10 heteroalkyl group, or a substituted or unsubstituted C3 to C20 heterocycloalkyl group, a structural unit represented by Chemical Formula 5 or Chemical Formula 6, or a combination thereof, in Chemical Formula 7, A may be a single bond, a substituted or unsubstituted C1 to C10 alkylene group, or a combination thereof, X may be a single bond, —O—, —S—, —S(=O)—, —S(=O)$_2$—, or a combination thereof, $R^d$ may be a substituted or unsubstituted C1 to C20 alkyl group, a substituted or unsubstituted C3 to C10 cycloalkyl group, a substituted or unsubstituted C1 to C30 thioalkyl group, or a combination thereof, and $R^e$ may be hydrogen, deuterium, a C1 to C10 alkyl group, or a combination thereof.

In some embodiments, $R^1$ and $R^2$ of Chemical Formula 1 may each independently be a hydroxy group, $L^1$ and $L^2$ of Chemical Formula 1 may each independently be a substituted or unsubstituted C1 to C10 alkylene group, a substituted or unsubstituted C6 to C20 arylene group, or a combination thereof, $R^3$ to $R^6$ of Chemical Formula 2 may each independently be a hydroxy group, and $L^3$ of Chemical Formula 2 may be a substituted or unsubstituted phenylene group.

In some embodiments, $R^a$ and $R^b$ of Chemical Formulae 3 and 4 may each independently be a substituted or unsubstituted C1 to C10 alkyl group, a substituted or unsubstituted C2 to C20 alkenyl group, or a combination thereof, $R^c$ of Chemical Formulae 3 and 4 may be a substituted or unsubstituted C1 to C10 alkyl group, a substituted or unsubstituted C1 to C10 heteroalkyl group, a structural unit represented by Chemical Formula 5 or Chemical Formula 6, or a combination thereof, in Chemical Formula 7, A may be a substituted or unsubstituted C1 to C5 alkylene group, X may be —S—, $R^d$ may be a substituted or unsubstituted C1 to C10 alkyl group, a substituted or unsubstituted C1 to C10 thioalkyl group, or a combination thereof, and $R^e$ may be a C1 to C10 alkyl group.

In some embodiments, the polymer including the structural unit represented by Chemical Formula 1 may include a structural unit represented by Chemical Formula 1-1, a structural unit represented by Chemical Formula 1-2, or a combination thereof:

Chemical Formula 1-1

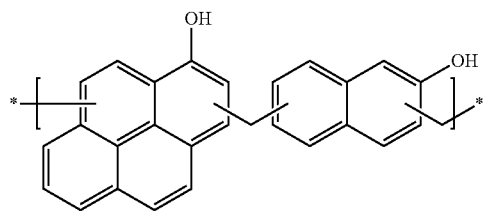

Chemical Formula 1-2

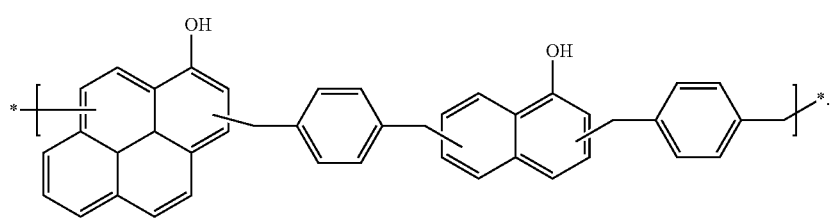

In Chemical Formulae 1-1 and 1-2,
* is a linking point.

In some embodiments, the compound represented by Chemical Formula 2 may be a compound represented by Chemical Formula 2-1:
Chemical Formula 2-1
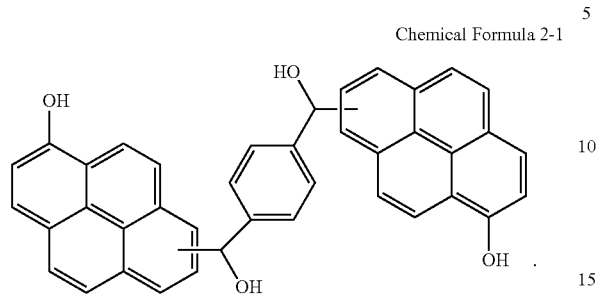
In some embodiments, the polymer (B) may be represented by any one of Chemical Formulae 3-1 to 3-5, or Chemical Formulae 4-1 to 4-5:
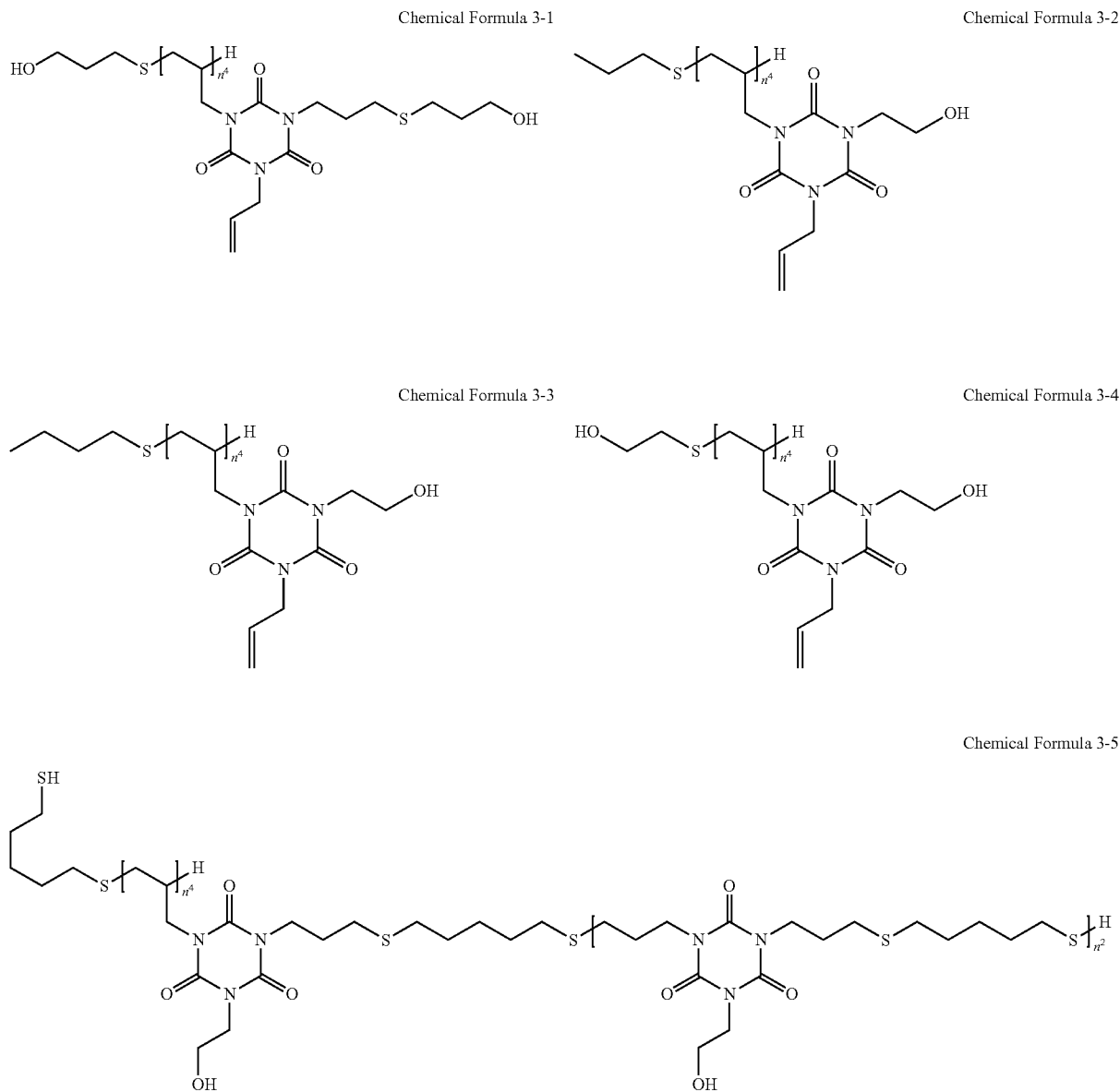

-continued

Chemical Formula 4-1

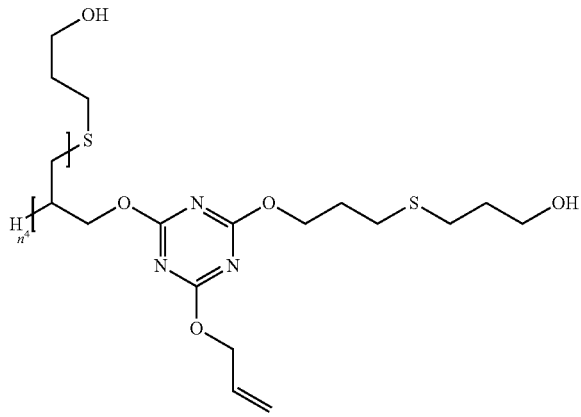

Chemical Formula 4-2

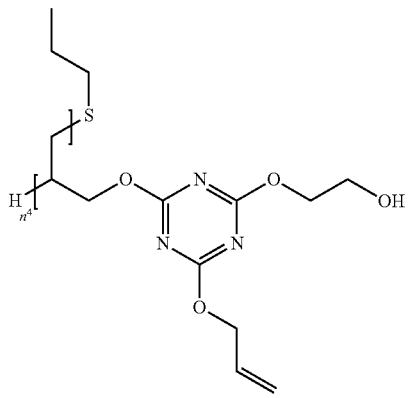

Chemical Formula 4-3

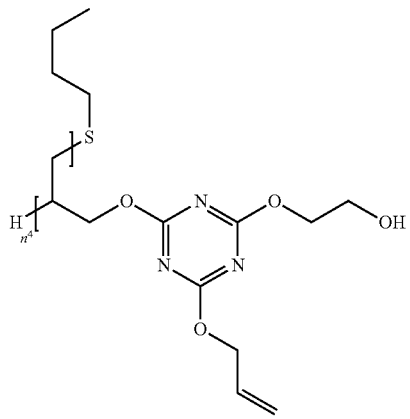

Chemical Formula 4-4

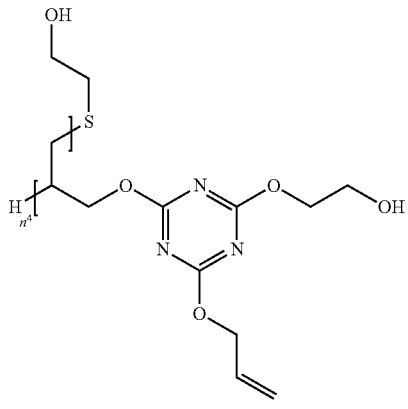

Chemical Formula 4-5

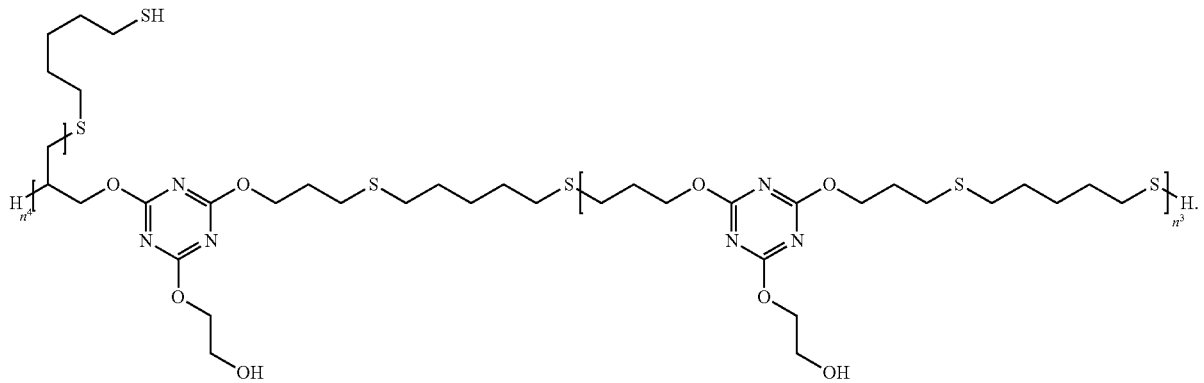

In Chemical Formulae 3-1 to 3-5, and Chemical Formulae 4-1 to 4-5, $n^4$ is 1 to 10,000, in Chemical Formula 3-5, $n^2$ is 1 to 10,000, and in Chemical Formula 4-5, $n^3$ is 1 to 10,000.

In some embodiments, the composition may include the polymer including a structural unit represented by Chemical Formula 1, the compound represented by Chemical Formula 2, or a combination thereof; and the polymer including the structure in which at least one of the moieties represented by Chemical Formula 3 or 4 and the moiety represented by Chemical Formula 7 are bound to each other, (e.g., (A) and (B)) in a weight ratio of about 80:20 to about 20:80.

In some embodiments, a weight average molecular weight of the polymer including the structural unit represented by Chemical Formula 1 may be about 1,000 g/mol to about 10,000 g/mol.

In some embodiments, a weight average molecular weight of the polymer including the structure in which at least one of the moieties represented by Chemical Formula 3 or 4 and the moiety represented by Chemical Formula 7 are bound to each other (e.g., (B)) may be about 2,000 g/mol to about 100,000 g/mol.

In some embodiments, a sum weight of the polymer including a structural unit represented by Chemical Formula 1, the compound represented by Chemical Formula 2, or a combination thereof (e.g., (A)); and the polymer including the structure in which at least one of the moieties represented by Chemical Formula 3 or 4 and the moiety represented by Chemical Formula 7 are bound to each other (e.g., (B)) may be about 0.01 wt % to about 5 wt % based on a total weight of the resist underlayer composition.

In some embodiments, the composition may further include at least one polymer selected from an acrylic resin, an epoxy resin, a novolac resin, a glycoluril resin, and a melamine resin.

In some embodiments, the composition may further include an additive including a surfactant, a thermal acid generator, a plasticizer, or a combination thereof.

One or more example embodiments of the present disclosure provide a method of forming patterns that includes:
  forming an etching target layer on the substrate,
  forming a resist underlayer by applying the resist underlayer composition according to an embodiment on the etching target layer,
  forming a photoresist pattern on the resist underlayer, and
  sequentially etching the resist underlayer layer and the etching target layer using the photoresist pattern as an etching mask.

In some embodiments, the forming of the photoresist pattern may include:
  forming a photoresist layer on the resist underlayer,
  exposing the photoresist layer, and
  developing the photoresist layer.

In some embodiments, the forming of the resist underlayer may further include heat treating the resist underlayer at a temperature of about 100° C. to about 500° C.

The resist underlayer composition according to an embodiment may form an ultra-thin film suitable for high energy rays (such as EUV and/or the like) and also (e.g., simultaneously), provide a resist underlayer having excellent coating properties, flattening properties, and/or adhesion to photoresists, as well as excellent chemical resistance to solutions used during the lithography process and a fast etch rate. Accordingly, the resist underlayer composition according to an embodiment, or the resist underlayer formed thereof may be advantageously used to form a fine pattern of a photoresist using a high energy light source (such as EUV and/or the like).

DETAILED DESCRIPTION

Figure 1:
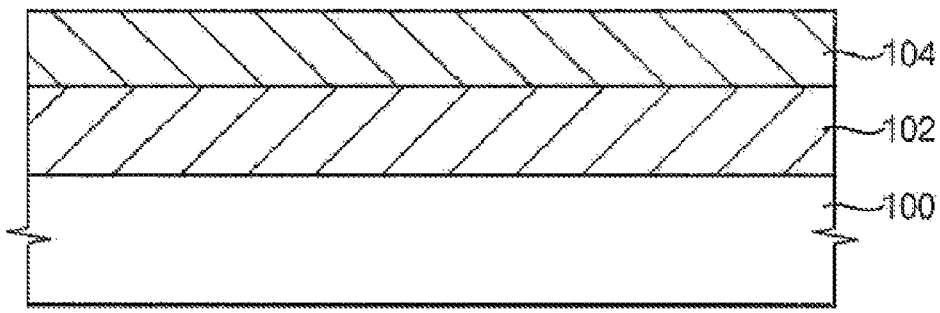
FIGS. 1 to 5 are cross-sectional views illustrating a method of forming patterns using a resist underlayer composition according to an embodiment.

Example embodiments of the present disclosure will hereinafter be described in more detail, and may be practiced by a person skilled in the art. However, this disclosure may be embodied in many different forms and should not be construed as limited to the example embodiments set forth herein.

In the drawings, the thickness of layers, films, panels, regions, etc., may be exaggerated for clarity, and like reference numerals designate like elements throughout the specification, such that duplicative descriptions thereof may not be provided. It will be understood that when an element such as a layer, film, region, or substrate is referred to as being "on" another element, it can be directly on the other element, or intervening elements may also be present. In contrast, when an element is referred to as being "directly on" another element, there are no intervening elements present.

As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, expressions such as "at least one of," "one of," and "selected from," when preceding a list of elements, modify the entire list of elements and do not modify the individual elements of the list. As used herein, the term "and/or" includes any and all combinations of one or more of the associated listed items. Further, the use of "may" when describing embodiments of the present disclosure refers to "one or more embodiments of the present disclosure".

As used herein, when a definition is not otherwise provided, the term "substituted" refers to replacement of at least one hydrogen atom of a compound or group with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a vinyl group, a C1 to C20 alkyl group, a C2 to C20 alkenyl group, a C2 to C20 alkynyl group, a C6 to C30 aryl group, a C7 to C30 arylalkyl group, a C6 to C30 allyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, the term "hetero" refers to the inclusion of one or more (e.g., 1 to 10 heteroatoms) selected from N, O, S, and P.

Unless otherwise specified in the present specification, the weight average molecular weight is measured by dissolving a powder sample in tetrahydrofuran (THF) and analyzing the resulting solution using a 1200 series Gel Permeation Chromatograph (GPC) by Agilent Technologies (equipped with a column by Shodex Company LF-804, standard sample is Shodex company polystyrene).

In addition, unless otherwise defined in the specification, "*" indicates a linking (connection) point of a structural unit or a moiety of a compound.

Hereinafter, a resist underlayer composition according to an embodiment is described.

Aspects of embodiments of the present disclosure provide a resist underlayer composition capable of reducing resist pattern collapse while forming a fine pattern in photolithography utilizing a short wavelength light source (such as an ArF excimer laser having a wavelength of 193 nm) or a high energy ray (such as EUV (extreme ultraviolet) having a wavelength of 13.5 nm). The resist underlayer composition may be capable of reducing an etching process time because it is applied with an ultra-thin film, and may be capable of improving the patterning of a photoresist due to improvement of sensitivity to an exposure light source. Additional aspects of embodiments of the present disclosure provide a method of forming a photoresist pattern using the underlayer.

A resist underlayer composition according to an embodiment includes: (A) a polymer including a structural unit represented by Chemical Formula 1, a compound represented by Chemical Formula 2, or a combination thereof; (B) a polymer including a structure in which at least one moiety represented by Chemical Formula 3 or Chemical Formula 4 and a moiety represented by Chemical Formula 7 are bound to each other; and (C) a solvent:

Chemical Formula 1

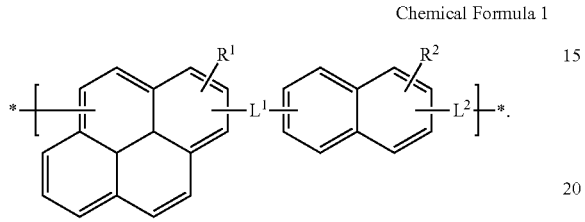

In Chemical Formula 1,
$R^1$ and $R^2$ may each independently be a hydroxy group, a substituted or unsubstituted C1 to C20 alkoxy group, a halogen, a substituted or unsubstituted C1 to C20 alkyl group, a substituted or unsubstituted C2 to C30 alkenyl group, a substituted or unsubstituted C2 to C20 alkynyl group, a substituted or unsubstituted C6 to C30 aryl group, a substituted or unsubstituted C6 to C30 heteroaryl group, a substituted or unsubstituted vinyl group, or a combination thereof, $L^1$ and $L^2$ may each independently be a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, and \* may be a linking point;

Chemical Formula 2

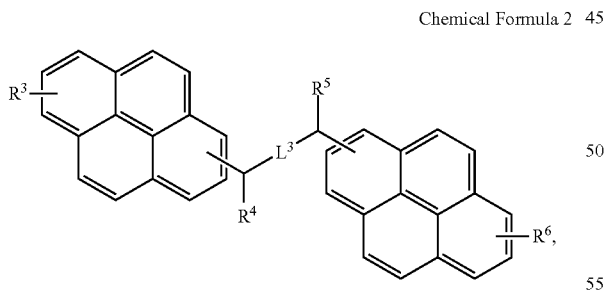

in Chemical Formula 2,
$R^3$ to $R^6$ may each independently be a hydroxy group, a thiol group, a cyano group, a substituted or unsubstituted amino group, a halogen atom, a substituted or unsubstituted C1 to C30 alkyl group, a substituted or unsubstituted C1 to C30 alkoxy group, a substituted or unsubstituted C6 to C30 aryl group, or a combination thereof, and $L^3$ may be a single bond, a substituted or unsubstituted C1 to C30 alkylene group, a substituted or unsubstituted C6 to C30 arylene group, or a combination thereof;

Chemical Formula 3

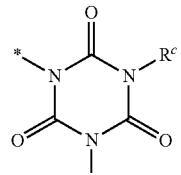

Chemical Formula 4

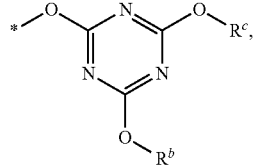

in Chemical Formulae 3 and 4,
$R^a$ and $R^b$ may each independently be hydrogen, deuterium, a substituted or unsubstituted C1 to C10 alkyl group, a substituted or unsubstituted C2 to C20 alkenyl group, a substituted or unsubstituted C2 to C20 vinyl group, a substituted or unsubstituted C2 to C20 alkynyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C2 to C20 heteroalkenyl group, a substituted or unsubstituted C3 to C20 heterocycloalkyl group, or a substituted or unsubstituted C6 to C20 heteroaryl group, or a combination thereof, $R^c$ is a terminal group that may be a substituted or unsubstituted C1 to C10 alkyl group, a substituted or unsubstituted C2 to C20 alkenyl group, a substituted or unsubstituted C2 to C20 alkynyl group, a substituted or unsubstituted C3 to C20 cycloalkyl group, a substituted or unsubstituted C1 to C10 heteroalkyl group, a substituted or unsubstituted C2 to C20 heteroalkenyl group, a substituted or unsubstituted C3 to C20 heterocycloalkyl group, a structural unit represented by Chemical Formula 5 or Chemical Formula 6, or a combination thereof, and the at least one moiety represented by Chemical Formula 3 or 4 is linked \* in Chemical Formula 7 at each \* position;

Chemical Formula 5

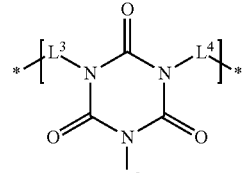

Chemical Formula 6

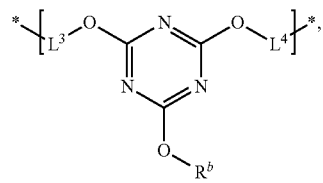

in Chemical Formulae 5 and 6, $L^3$ and $L^4$ may each independently be a substituted or unsubstituted C1 to C20 alkylene group, a substituted or unsubstituted C1 to C20 heteroalkylene group, or a combination thereof, $R^a$ and $R^b$ may each independently be the same as defined in Chemical Formula 3 and Chemical Formula 4, and \* is a linking point; and

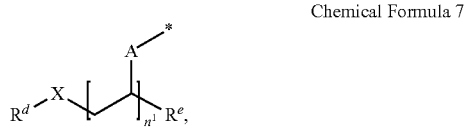

Chemical Formula 7 in Chemical Formula 7,

A may be a single bond, a substituted or unsubstituted C1 to C10 alkylene group, —C(=O)—, —(CO)O—, —O(CO)O—, or a combination thereof, X may be a single bond, —O—, —S—, —S(=O)—, —S(=O)$_2$—, —C(=O)—, —(CO)O—, —O(CO)O—, —NR— (wherein R is hydrogen, deuterium, or a C1 to C10 alkyl group), or a combination thereof, $R^d$ may be hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, $R^e$ may be one of hydrogen, deuterium, or a C1 to C10 alkyl group, $n^1$ may be 1 to 10,000 (e.g., an integer from 1 to 10,000), and \* is linked to Chemical Formula 3 or Chemical Formula 4, or linked to hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, provided that at least one of Chemical Formula 3 or Chemical Formula 4 is linked to \* of Chemical Formula 7.

The composition according to an embodiment is coated at the bottom of (e.g. under) a photoresist and forms a film, and thus may improve close contacting properties between the film and the photoresist and prevent or reduce collapse of the resist pattern even during a fine patterning process, In addition, the composition according to an embodiment may enhance sensitivity to an exposure light source and thus improve the patterning performance and/or the efficiency of the photoresist. In addition, the composition may form an ultra-thin underlayer film and thus shorten the duration of the etching process.

Among the polymers included in the composition, the polymer (A) including the structural unit represented by Chemical Formula 1 or the compound represented by Chemical Formula 2 includes a substituted polycyclic aromatic ring group capable of improving film density. For example, the polymer including the structural unit represented by Chemical Formula 1 or the compound represented by Chemical Formula 2 includes a pyrene structure, which is a polycyclic aromatic ring group with high electron density, so that a densely-structured film may be implemented in the form of an ultra-thin film, and when a pattern is formed after exposure to high energy rays (such as EUV (Extreme UltraViolet) having a wavelength of 13.5 nm), e-beam (electron beam), and/or the like), energy efficiency may be improved.

The polymer (B) including a structure in which at least one moiety represented by Chemical Formula 3 or 4 and a moiety represented by Chemical Formula 7 are bound to each other includes an isocyanurate backbone or a triazine backbone and may thus exhibit a suitable etch selectivity ratio. In addition, the polymer (B) may include a sulfur (S) atom, and may thus exhibit a relatively high refractive index and fast etch rate.

In addition, the polymer including the moieties (e.g., the polymer (B)) may be selectively substituted with various suitable functional groups so that adhesion to the photoresist may be suitably adjusted or controlled in order to suppress pattern collapses during the process of forming the pattern, and in some embodiments, the suitable functional groups may provide an increased crosslinking rate to thereby improve the film density and chemical resistance.

The moiety represented by Chemical Formula 7 may improve the solubility of the polymer including the same (e.g., the polymer (B)) due to the flexible backbone structure. In addition, the isocyanurate or triazine unit may be densely present in the polymer and may thus help the film density and ultra-thin coating properties of the resist underlayer.

Accordingly, the resist underlayer composition according to an embodiment may form a resist underlayer with improved adhesion and chemical resistance and a reduced thickness, through which faster etching may be achieved compared with the upper photoresist, and the absorption efficiency of the exposure light source may be improved, thereby improving patterning performance.

In an embodiment, $R^1$ and $R^2$ of Chemical Formula 1 may each independently be a hydroxy group, a substituted or unsubstituted C1 to C20 alkoxy group, a substituted or unsubstituted C1 to C20 alkyl group, a substituted or unsubstituted C6 to C30 aryl group, a substituted or unsubstituted vinyl group, or a combination thereof, $L^1$ and $L^2$ may each independently be a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, $R^3$ to $R^6$ of Chemical Formula 2 may each independently be a hydroxy group, a thiol group, a cyano group, a substituted or unsubstituted C1 to C30 alkoxy group, or a combination thereof, and L³ may be a substituted or unsubstituted phenylene group, a substituted or unsubstituted naphthalenylene group, a substituted or unsubstituted biphenylene group, or a combination thereof.

In an embodiment, $R^a$ and $R^b$ of Chemical Formulae 3 and 4 may each independently be a substituted or unsubstituted C1 to C10 alkyl group, a substituted or unsubstituted C2 to C20 alkenyl group, a substituted or unsubstituted C3 to C20 cycloalkyl group, a substituted or unsubstituted C1 to C10 heteroalkyl group, a substituted or unsubstituted C2 to C20 heteroalkenyl group, or a substituted or unsubstituted C3 to C20 heterocycloalkyl group, $R^c$ may be a terminal group that is a substituted or unsubstituted C1 to C10 alkyl group, a substituted or unsubstituted C3 to C20 cycloalkyl group, a substituted or unsubstituted C1 to C10 heteroalkyl group, a substituted or unsubstituted C3 to C20 heterocycloalkyl group, a structural unit represented by Chemical Formula 5 or Chemical Formula 6, or a combination thereof, in Chemical Formula 7, A may be a single bond, a substituted or unsubstituted C1 to C10 alkylene group, or a combination thereof, X may be a single bond, —O—, —S—, —S(=O)—, —S(=O)₂—, or a combination thereof, $R^d$ may be a substituted or unsubstituted C1 to C20 alkyl group, a substituted or unsubstituted C3 to C10 cycloalkyl group, a substituted or unsubstituted C1 to C30 thioalkyl group, or a combination thereof, and $R^e$ may be hydrogen, deuterium, a C1 to C10 alkyl group, or a combination thereof.

In an embodiment, $R^1$ and $R^2$ of Chemical Formula 1 may each independently be a hydroxy group, $L^1$ and $L^2$ may each independently be a substituted or unsubstituted C1 to C10 alkylene group, a substituted or unsubstituted C6 to C20 arylene group, or a combination thereof, $R^3$ to $R^6$ of Chemical Formula 2 may each independently be a hydroxy group, and $L^3$ of Chemical Formula 2 may be a substituted or unsubstituted phenylene group.

In an embodiment, $R^a$ and $R^b$ of Chemical Formulae 3 and 4 may each independently be a substituted or unsubstituted C1 to C10 alkyl group, a substituted or unsubstituted C2 to C20 alkenyl group, or a combination thereof, $R^c$ may be a substituted or unsubstituted C1 to C10 alkyl group, a substituted or unsubstituted C1 to C10 heteroalkyl group, a structural unit represented by Chemical Formula 5 or Chemical Formula 6, or a combination thereof, in Chemical Formula 7, A may be a substituted or unsubstituted C1 to C5 alkylene group, and X may be —S—, $R^d$ may be a substituted or unsubstituted C1 to C10 alkyl group, a substituted or unsubstituted C1 to C10 thioalkyl group, or a combination thereof, and $R^e$ may be a C1 to C10 alkyl group.

In an embodiment, the polymer including a structural unit represented by Chemical Formula 1 may include a structural unit represented by Chemical Formula 1-1, a structural unit represented by Chemical Formula 1-2, or a combination thereof:

Chemical Formula 1-1

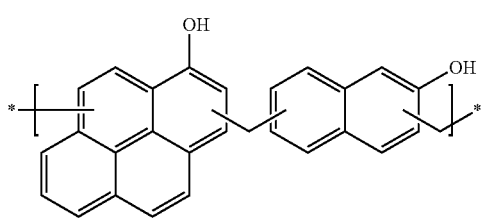

Chemical Formula 1-2

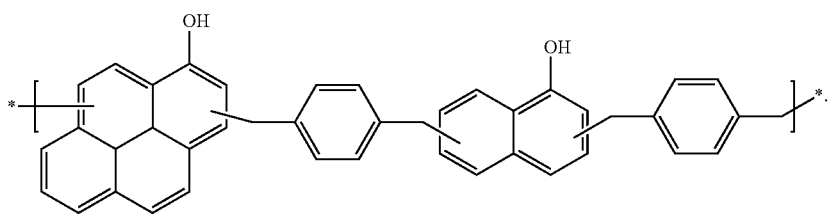

In Chemical Formulae 1-1 and 1-2,

* is a linking point.

In some embodiments, the compound represented by Chemical Formula 2 may be a compound represented by Chemical Formula 2-1.

Chemical Formula 2-1

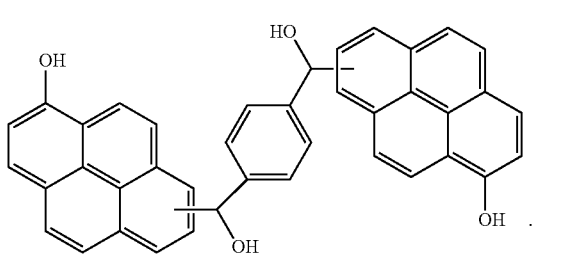

In an embodiment, the polymer (B) may be represented by any one of Chemical Formulae 3-1 to 3-5, or Chemical Formulae 4-1 to 4-5.

Chemical Formula 3-1
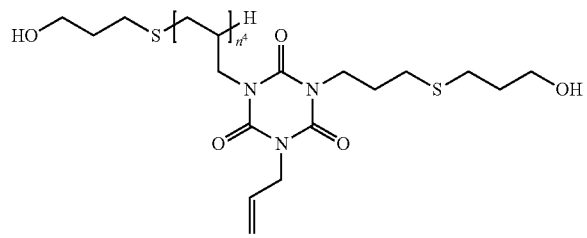
Chemical Formula 3-2
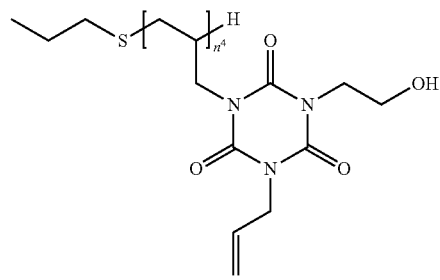
Chemical Formula 3-3
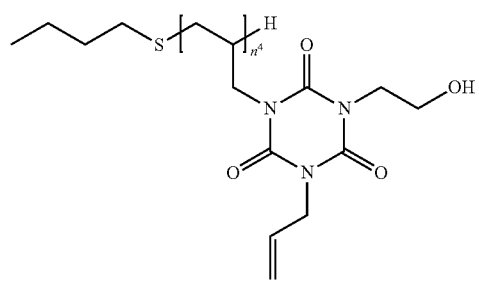
Chemical Formula 3-4
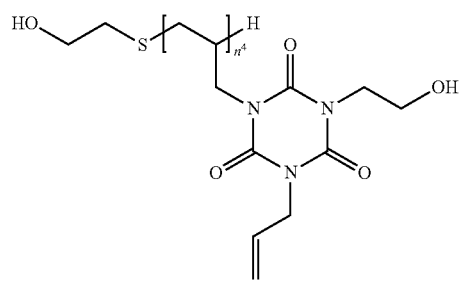
Chemical Formula 3-5
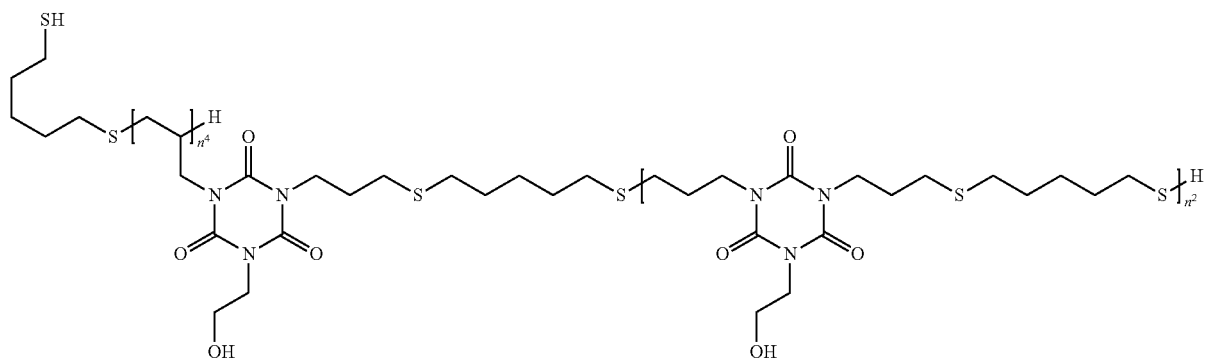
Chemical Formula 4-1
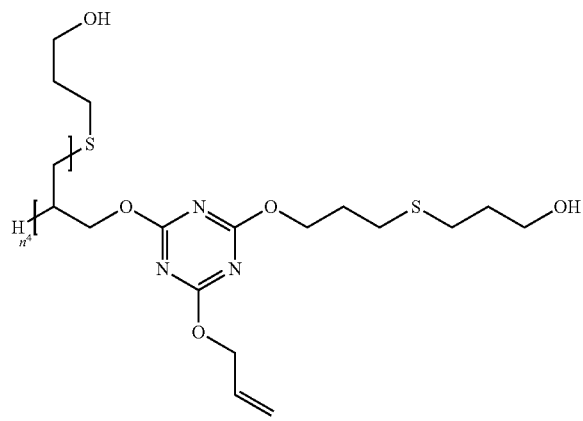
Chemical Formula 4-2
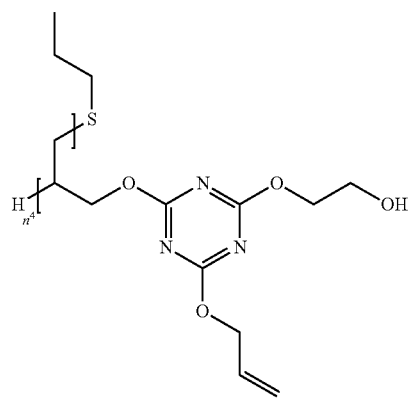

Chemical Formula 4-3

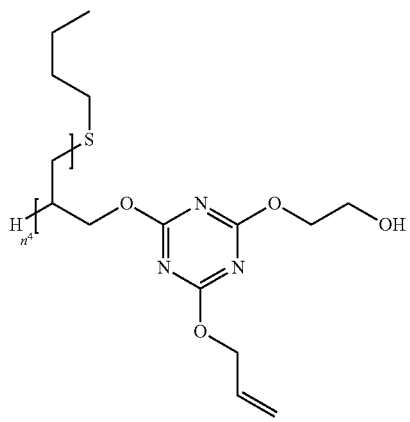

Chemical Formula 4-4

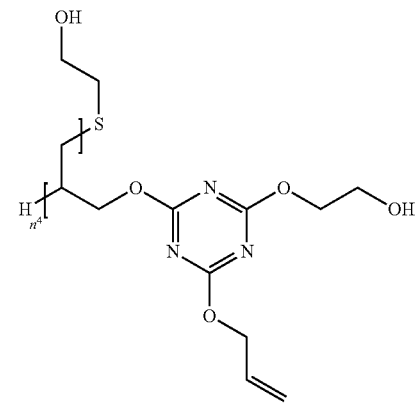

Chemical Formula 4-5

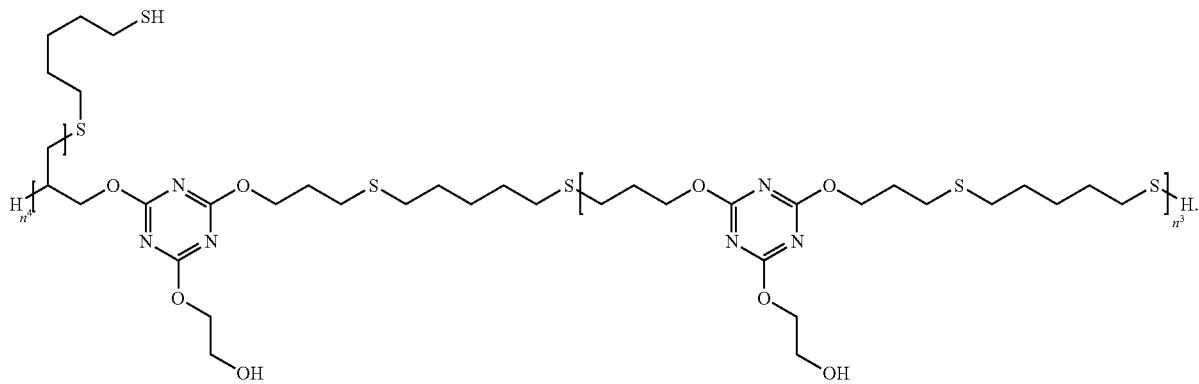

In Chemical Formulae 3-1 to 3-5 and Chemical Formulae 4-1 to 4-5, $n^4$ may be 1 to 10,000 (e.g., an integer from 1 to 10,000), in Chemical Formula 3-5, $n^2$ may be 1 to 10,000 (e.g., an integer from 1 to 10,000), and in Chemical Formula 4-5, $n^3$ may be 1 to 10,000 (e.g., an integer from 1 to 10,000).

The composition may include the polymer (A) including a structural unit represented by Chemical Formula 1, the compound represented by Chemical Formula 2, or a combination thereof; and the polymer (B) including the structure in which at least one moiety represented by Chemical Formula 3 or 4 and the moiety represented by Chemical Formula 7 are bound to each other, in a weight ratio of about 80:20 to about 20:80, for example about 75:25 to about 25:75, about 70:30 to about 30:70, about 65:35 to about 35:65, about 60:40 to about 40:60, or about 55:45 to about 45:55, but is not limited thereto. When the polymer (A) and the polymer (B) are included within the above weight ratios, the resist underlayer composition according to an embodiment may provide a resist underlayer having an improved quality due to improved adhesion to the photoresist and a suitable film density.

The polymer (A) including a structural unit represented by Chemical Formula 1 may have a weight average molecular weight (Mw) of about 1,000 g/mol to about 10,000 g/mol. For example, the polymer including a structural unit represented by Chemical Formula 1 may have a weight average molecular weight of about 2,000 g/mol to about 8,000 g/mol, for example about 3,000 g/mol to about 7,000 g/mol, or about 4,000 g/mol to about 5,000 g/mol, but is not limited thereto. When the weight average molecular weight of the polymer including the structural unit represented by Chemical Formula 1 is less than about 1,000 g/mol, the film density of the resist underlayer produced from it decreases, and the photoresist pattern may be damaged or collapsed during the patterning process, so that stability may be deteriorated.

The polymer (B) including the structure in which at least one moiety represented by Chemical Formula 3 or 4 and the moiety represented by Chemical Formula 7 are bound to each other may have a weight average molecular weight of about 2,000 g/mol to about 100,000 g/mol, for example, about 5,000 g/mol to about 100,000 g/mol, about 10,000 g/mol to about 100,000 g/mol, about 20,000 g/mol to about 100,000 g/mol, about 30,000 g/mol to about 100,000 g/mol, about 40,000 g/mol to about 100,000 g/mol about 50,000 g/mol to about 80,000 g/mol, or about 50,000 g/mol to about 70,000 g/mol, but is not limited thereto. When the weight average molecular weight is within the above range, the carbon content and solubility in a solvent of the resist underlayer composition including the polymer may be adjusted and thus optimized.

A sum weight of the polymer (A) including a structural unit represented by Chemical Formula 1, the compound represented by Chemical Formula 2, or a combination thereof; and the polymer (B) including the structure in which at least one moiety represented by Chemical Formula 3 or 4 and the moiety represented by Chemical Formula 7 are bound to each other may be about 0.01 wt % to about 5 wt % based on a total weight of the resist underlayer composition. Within the above ranges, the thickness, surface roughness, and degree of planarization of the resist underlayer may be suitably adjusted or selected.

In some embodiments, the resist underlayer composition may further include at least one other polymer selected from an acrylic resin, an epoxy resin, a novolac resin, a glycoluril resin, and a melamine resin, (in addition to the polymers described above), but is not limited thereto.

The resist underlayer composition may further include an additive including a surfactant, a thermal acid generator, a plasticizer, or a combination thereof.

The surfactant may be, for example, an alkylbenzene sulfonate salt, an alkylpyridinium salt, polyethylene glycol, a quaternary ammonium salt, and/or the like, but is not limited thereto.

The thermal acid generator may be an acidic compound (such as p-toluene sulfonic acid, trifluoromethanesulfonic acid, pyridinium p-toluene sulfonic acid, salicylic acid, sulfosalicylic acid, citric acid, benzoic acid, hydroxybenzoic acid, naphthalene carbonic acid, benzoin tosylate, 2-nitrobenzyltosylate, and/or any suitable organic sulfonic acid alkylester), but is not limited thereto.

The additive may be included in an amount of about 0.001 parts by weight to about 40 parts by weight based on 100 parts by weight of the resist underlayer composition. Within the above range, solubility may be improved without changing the optical properties of the resist underlayer composition.

The solvent is not particularly limited as long as it has sufficient solubility or dispersibility in the polymer, and may include, for example, at least one selected from propylene glycol, propylene glycol diacetate, methoxy propanediol, diethylene glycol, diethylene glycol butylether, tri(ethylene glycol)monomethylether, propylene glycol monomethylether, propylene glycol monomethylether acetate, cyclohexanone, ethyl lactate, gamma-butyrolactone, N,N-dimethyl formamide, N,N-dimethyl acetamide, methylpyrrolidone, methylpyrrolidinone, methyl 2-hydroxyisobutyrate, acetylacetone, and ethyl 3-ethoxypropionate.

In addition, the resist underlayer composition may further include a crosslinking agent.

The crosslinking agent may be, for example a melamine-based, substituted urea-based, or a polymer-based crosslinking agent. In some embodiments, the crosslinking agent may have at least two crosslinking substituents, for example, methoxymethylated glycoruryl, butoxymethylated glycoruryl, methoxymethylated melamine, butoxymethylated melamine, methoxymethylated benzoguanamine, butoxy methylated benzoguanamine, methoxymethylated urea, butoxymethylated urea, methoxymethylated thiourea, butoxymethylated thiourea, and/or the like.

The crosslinking agent having high heat resistance may be a compound including a crosslinking substituent including an aromatic ring (for example a benzene ring and/or a naphthalene ring). The crosslinking agent may have, for example, two or more crosslinking sites.

According to another embodiment, a resist underlayer may be prepared by utilizing the aforementioned resist underlayer composition. The resist underlayer may be formed by coating the aforementioned resist underlayer composition on, for example, a substrate, and then curing through a heat treatment process.

Hereinafter, a method of forming a pattern using the aforementioned resist underlayer composition is described with reference to FIGS. 1 to 5.

FIGS. 1 to 5 are cross-sectional views illustrating a method of forming a pattern using the resist underlayer composition according to the present disclosure.

Referring to FIG. 1, an etching target is prepared. The etching target may be a thin film 102 formed on a semiconductor substrate 100. Hereinafter, the etching target is limited to the thin film 102. An entire surface of the thin film 102 is washed to remove impurities and the like remaining thereon. The thin film 102 may be, for example, a silicon nitride layer, a polysilicon layer, or a silicon oxide layer.

Subsequently, the resist underlayer composition including the polymer having moieties represented by Chemical Formulae 1 and 2 and the solvent is coated on the surface of the cleaned thin film 102 by applying a spin coating method.

Then, the coated composition is dried and baked to form a resist underlayer 104 on the thin film 102. The baking may be performed at about 100° C. to about 500° C., for example, about 100° C. to about 300° C. The resist underlayer composition is described above in detail.

Figure 2:
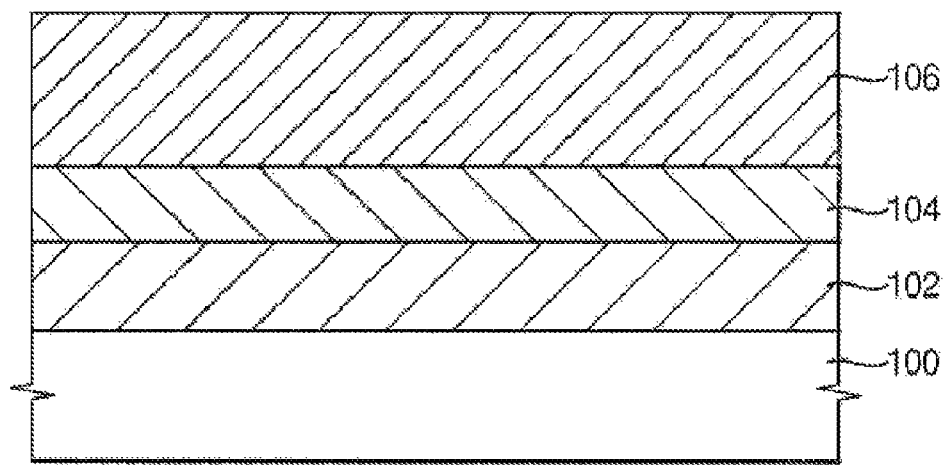

Referring to FIG. 2, a photoresist layer 106 is formed by coating a photoresist on the resist underlayer 104.

Examples of the photoresist include a positive-type photoresist containing a naphthoquinonediazide compound and a novolac resin, a chemically-amplified positive photoresist containing an acid generator capable of dissociating acid through exposure, a compound decomposed under presence of acid and having increased dissolubility in an alkali aqueous solution, an alkali soluble resin, a chemically-amplified positive-type photoresist containing an alkali-soluble resin capable of applying a resin increasing dissolubility in an alkali aqueous solution, and/or the like.

Then, a substrate 100 having the photoresist layer 106 is primarily baked (e.g., baked in a primary baking process). The primary baking may be performed at about 90° C. to about 120° C.

Figure 3:
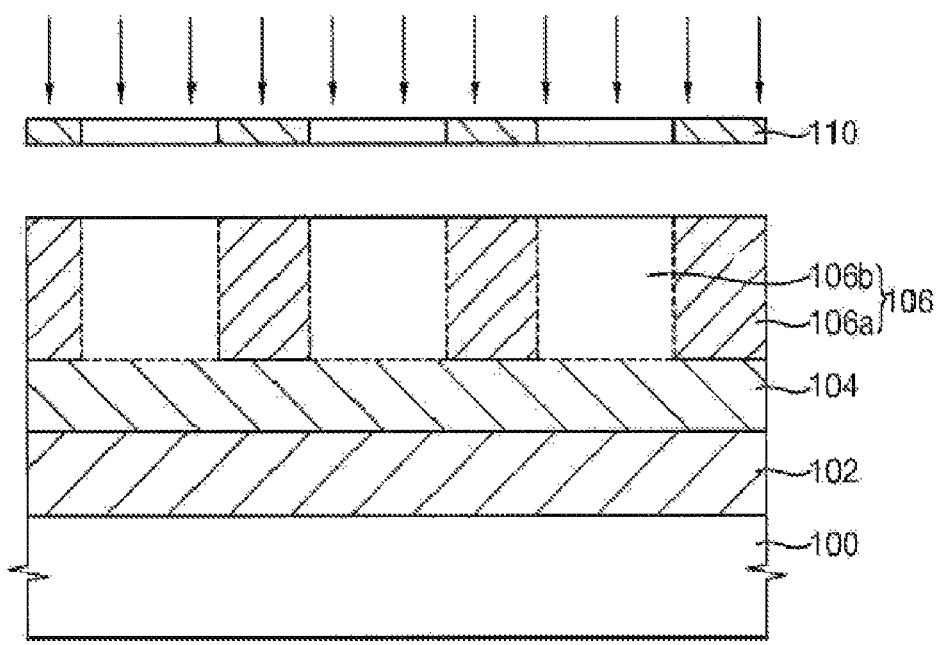

Referring to FIG. 3, the photoresist layer 106 may be selectively exposed.

Exposure of the photoresist layer 106 may be, for example, performed by positioning an exposure mask 110 having a set or predetermined pattern on a mask stage of an exposure apparatus and aligning the exposure mask 110 on (over) the photoresist layer 106. Subsequently, a set or predetermined region of the photoresist layer 106 formed on the substrate 100 (e.g., a region of the photoresist layer 106 exposed by the exposure mask 110) selectively reacts with light upon light irradiation through the exposure mask 110.

For example, the light used during the exposure may include short wavelength light (such as an activated irradiation i-line having a wavelength of 365 nm, a KrF excimer laser having a wavelength of 248 nm, and/or an ArF excimer laser having a wavelength of 193 nm). In some embodiments, EUV (extreme ultraviolet) light having a wavelength of 13.5 nm may be used.

The exposed region 106b of the photoresist layer is relatively hydrophilic compared with the unexposed region 106a of the unexposed region. Accordingly, the exposed region 106b and non-exposed region 106a of the photoresist layer 106 may have different solubilities from each other.

Subsequently, the substrate 100 is secondarily baked (e.g., baked in a secondary baking process). The secondary baking may be performed at about 90° C. to about 150° C. The exposed region 106b of the photoresist layer may then become easily soluble in a set predetermined solvent due to the secondary baking.

Figure 4:
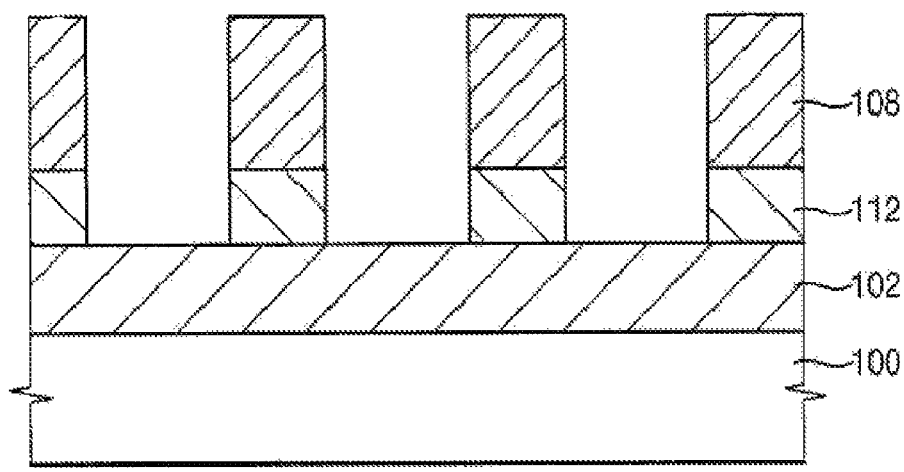

Referring to FIG. 4, the exposed region 106b of the photoresist layer is dissolved and removed by a developing solution to form a photoresist pattern 108. For example, the exposed region 106b of the photoresist layer is dissolved and removed by utilizing a developing solution (such as tetramethyl ammonium hydroxide (TMAH) and/or the like) to finish (provide) the photoresist pattern 108.

Subsequently, the photoresist pattern 108 is used as an etching mask to etch the resist underlayer. Through the etching, an organic layer pattern 112 is formed. The etching may be, for example, dry etching using etching gas, and the etching gas may be, for example, $CHF_3$, $CF_4$, $Cl_2$, $O_2$, or a mixed gas thereof. As described above, since the resist underlayer formed by the resist underlayer composition according to the embodiment has a fast etch rate, a smooth etching process may be performed within a short time.

Figure 5:
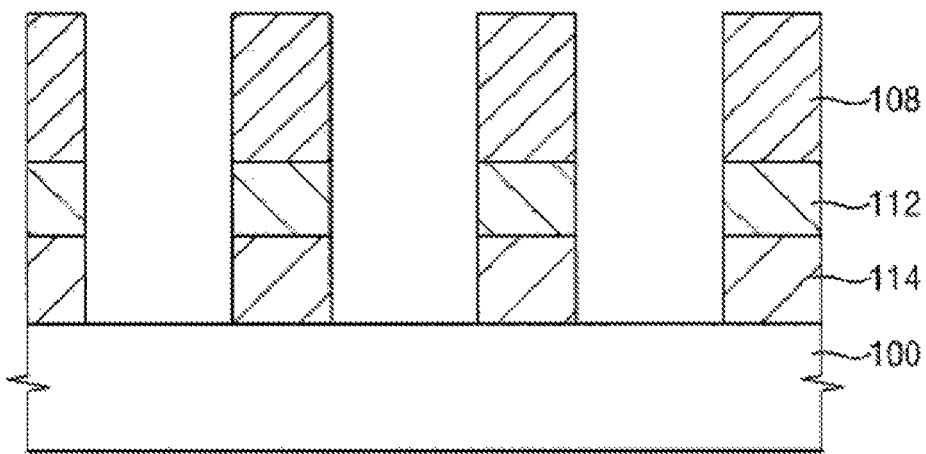

Referring to FIGS. 4 and 5, the photoresist pattern 108 is applied as an etching mask to etch the exposed thin film 102. As a result, the thin film is formed into a thin film pattern 114. In this regard, a thin film pattern formed by an exposure process utilizing a short wavelength light source, such as, for example, an activated irradiation i-line (a wavelength of 365 nm), a KrF excimer laser (a wavelength of 248 nm), an ArF excimer laser (a wavelength of 193 nm), and/or the like may have a width of tens to hundreds of nm, while a thin film pattern formed by an exposure process utilizing an EUV light source may have a width of less than or equal to about 20 nm.

Hereinafter, the present disclosure is described in more detail through Examples regarding synthesis of the polymer and preparation of a resist underlayer composition including the same. However, the present disclosure is technically not restricted by the following example embodiments.

SYNTHESIS EXAMPLES

Synthesis Example 1

14.4 g of 2-hydroxy naphthylene, 21.8 g of 1-hydroxy pyrene, 6 g of p-formaldehyde, 1.9 g of p-toluene sulfonic acid, and 100 g of propylene glycol monomethylether acetate were added to a flask and stirred at 85° C. for 10 hours. When a reaction was complete, methanol and water were added thereto, and the precipitates formed therein were repeatedly filtered to remove any excess starting monomers and to thereby isolate a polymer including a structural unit represented by Chemical Formula 1aa (weight average molecular weight (Mw)=3,500 g/mol).

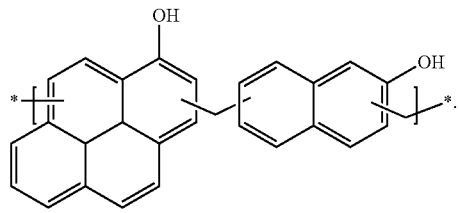

Chemical Formula 1aa

In Chemical Formula 1aa, * is a linking point.

Synthesis Example 2

14.4 g of 1-hydroxy naphthalene, 21.8 g of 1-hydroxy pyrene, 33.2 g of 1,4-bis(methoxymethyl)benzene, 1.5 g of diethyl sulfate, and 50 g of propylene glycol monomethylether acetate were added to a flask and stirred at 100° C. for 8 hours. When a reaction was complete, hexane, methanol, and water were added thereto to remove any monomers through precipitation and to thereby isolate a polymer including a structural unit represented by Chemical Formula 1 bb (a weight average molecular weight (Mw)=6,000 g/mol).

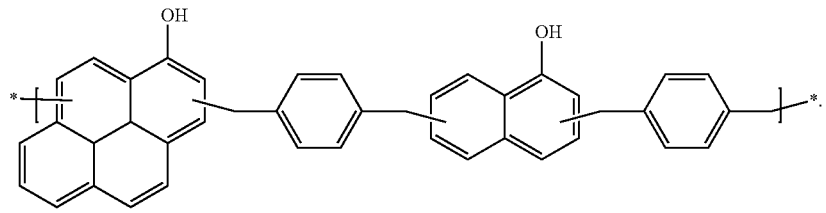

Chemical Formula 1bb

In Chemical Formula 1bb, * is a linking point.

Synthesis Example 3

First Step: Friedel-Craft Acylation Reaction 27.3 g of 1,4-benzene dicarbonyl chloride, 65.5 g of 1-methoxypyrene, and 496 g of 1,2-dichloroethane were added to a flask. Subsequently, 17.9 g of aluminum chloride was slowly added to this solution, and the reaction was stirred at room temperature for 12 hours. When the reaction was complete, methanol was added thereto, and the precipitates formed therein were filtered and dried.

Second Step: Demethylation Reaction 6.00 g of the compound, 10.13 g of 1-dodecanethiol, 3.37 g of potassium hydroxide, and 30.3 g of N,N-dimethylformamide were added to a flask and stirred at 120° C. for 8 hours. The reaction mixture was cooled down and neutralized to pH 6 to 7 utilizing a 5% hydrochloric acid solution, and the precipitates formed therein were filtered and dried.

Third Step: Reduction Reaction 4.00 g of the demethylated compound and 28.5 g of tetrahydrofuran were added to the flask. 5.29 g of a sodium borohydride aqueous solution was slowly added thereto, and the reaction was stirred at room temperature for 24 hours.

When the reaction was complete, the resultant was neutralized to about pH 7 utilizing a 5% hydrochloric acid solution, and then extracted with ethyl acetate and dried to obtain a compound represented by Chemical Formula 2aa.

Chemical Formula 2aa

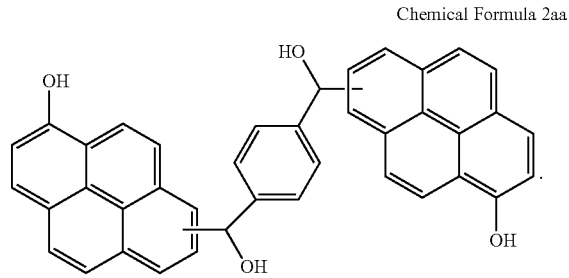

Synthesis Example 4

24.9 g of 1,3,5-triallyl-1,3,5-triazinane-2,4,6-trione, 8.4 g of 5-mercapto pentenol, 2.3 g of AIBN (azobisisobutyronitrile), and 15.9 g of N,N-dimethyl formamide (DMF) were added to a 500 mL 3-neck round flask, and a condenser was connected thereto. The obtained mixture was reacted at 80° C. for 16 hours, and then cooled down to room temperature. The reaction solution was added dropwise to a 1 L wide-mouthed bottle containing 800 g of water, while stirred, to produce a gum, and the gum was dissolved in 80 g of tetrahydrofuran (THF). The dissolved resin solution was treated with toluene to form precipitates and thereby remove any monomers and small molecules. Finally, 15 g of a polymer including a structural unit represented by Chemical Formula 3aa (a weight average molecular weight (Mw)=20,000 g/mol) was obtained.

Chemical Formula 3aa

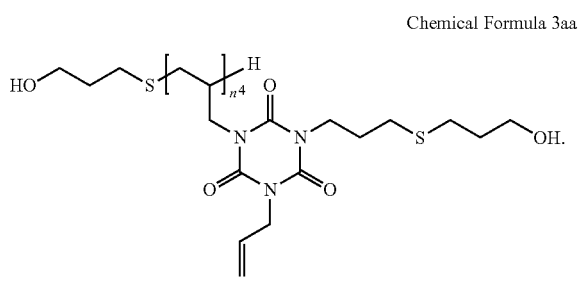

Synthesis Example 5

25.3 g of 1,3-diallyl-5-(2-hydroxyethyl) isocyanurate, 5.3 g of propane-1-thiol, 1.3 g of AIBN (azobisisobutyronitrile), and 15.9 g of N,N-dimethyl formamide (DMF) were added to a 500 mL 3-neck round flask, and a condenser was connected thereto. After reacting the mixture at 80° C. for 25 hours, the reaction solution was cooled down to room temperature. The reaction solution was added dropwise to a 1 L wide-mouthed bottle containing 800 g of water, while stirred, to produce a gum, and the gum was dissolved in 80 g of tetrahydrofuran (THF). The dissolved resin solution was treated with toluene to form precipitates and thereby remove any monomers and small molecules. Finally, 15 g of a polymer including a structural unit represented by Chemical Formula 3bb (a weight average molecular weight (Mw)=6,000 g/mol) was obtained.

Chemical Formula 3bb

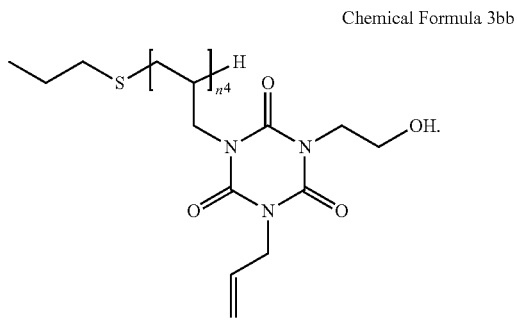

Synthesis Example 6

25.3 g of 1,3-diallyl-5-(2-hydroxyethyl) isocyanurate, 7.3 g of butane-1-thiol, 1.3 g of AIBN (azobisisobutyronitrile), and 15.9 g of N,N-dimethyl formamide (DMF) were added to n a 500 mL 2-necked round flask, and a condenser was connected thereto. The reaction solution was reacted at 80° C. for 25 hours, and then cooled down to room temperature. Subsequently, the reaction solution was added dropwise to a 1 L wide-mouthed bottle containing 800 g of water, while stirred, to produce a gum, and the gum was dissolved in 80 g of tetrahydrofuran (THF). The dissolved resin solution was treated with toluene to form precipitates and thereby remove any monomers and small molecules. Finally, 15 g of a polymer including a structural unit represented by Chemical Formula 3cc (a weight average molecular weight (Mw)=9,000 g/mol) was obtained.

Chemical Formula 3cc

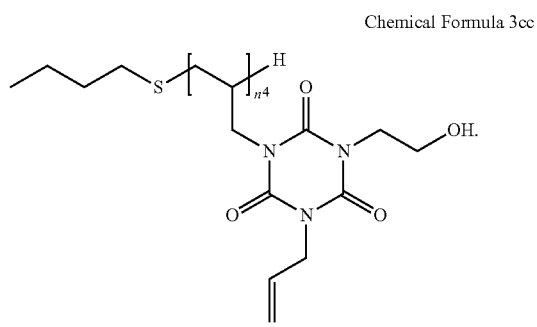

Synthesis Example 7

25.3 g of 1,3-diallyl-5-(2-hydroxyethyl) isocyanurate, 3.9 g of 2-mercapto ethanol, 1.3 g of AIBN (azobisisobutyronitrile), and 15.9 g of N,N-dimethyl formamide (DMF) were added to a 500 mL 2-necked round flask, and a condenser was connected thereto. The reaction solution was reacted at 80° C. for 25 hours, and then cooled down to room temperature. Subsequently, the reaction solution was added dropwise to a 1 L wide-mouthed bottle containing 800 g of water to produce a gum, and the gum was dissolved in 80 g of tetrahydrofuran (THF). The dissolved resin solution was treated using toluene to form precipitates and thereby remove any monomers and small molecules. Finally, 15 g of a polymer including a structural unit represented by Chemical Formula 3dd (a weight average molecular weight (Mw)= 7,000 g/mol) was obtained.

Chemical Formula 3dd structural unit represented by Chemical Formula 3ee (a weight average molecular weight (Mw)=3,500 g/mol) was obtained.

Chemical Formula 3ee

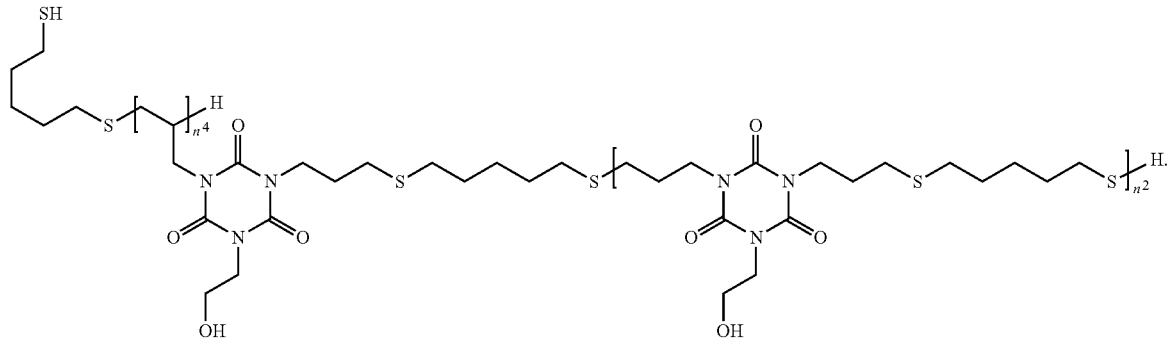

Synthesis Example 8

25.3 g of 1,3-diallyl-5-(2-hydroxyethyl) isocyanurate, 10.9 g of 1,5-pentanedithiol, 1.3 g of AIBN (azobisisobutyronitrile), and 15.9 g of N,N-dimethyl formamide (DMF) were added to a 500 mL 2-necked round flask, and a condenser was connected thereto. The obtained mixture was reacted at 80° C. for 16 hours, and 3.9 g of 2-mercaptopropanol and 1.3 g of AIBN (azobisisobutyronitrile) were added thereto, reacted for 8 hours, and then cooled down to room temperature. The reaction solution was dripped into a 1 L wide-mouthed bottle containing 800 g of water to produce a gum, and the gum was dissolved in 80 g of tetrahydrofuran (THF). The dissolved resin solution was treated with toluene to form precipitates and thereby remove any monomers and small molecules. Finally, 15 g of a polymer including a Preparation of Resist Underlayer Composition Examples 1 to 9 and Comparative Examples 1 to 2

0.5 g of the polymers (or the compounds) according to Synthesis Example 1 to 8 in the ratios shown in Table 1, 0.125 g of PD1174 (a hardener; TCI), and 0.01 g of pyridinium para-toluene sulfonate (PPTS) were completely dissolved in a mixed solvent of propylene glycol monomethylether and ethyl lactate (in a volume ratio=7:3) to prepare resist underlayer compositions according to Examples 1 to 9 and Comparative Examples 1 to 2.

TABLE 1

| | Polymer A (or compound) | Polymer B | Weight ratio |
|---|---|---|---|
| Example 1 | Synthesis Example 1 | Synthesis Example 4 | 20:80 |
| Example 2 | Synthesis Example 2 | Synthesis Example 4 | 70:30 |
| Example 3 | Synthesis Example 3 | Synthesis Example 4 | 70:30 |
| Example 4 | Synthesis Example 2 | Synthesis Example 5 | 80:20 |
| Example 5 | Synthesis Example 2 | Synthesis Example 5 | 50:50 |
| Example 6 | Synthesis Example 2 | Synthesis Example 5 | 30:70 |
| Example 7 | Synthesis Example 1 | Synthesis Example 6 | 50:50 |
| Example 8 | Synthesis Example 1 | Synthesis Example 7 | 50:50 |
| Example 9 | Synthesis Example 2 | Synthesis Example 8 | 40:60 |
| Comparative Example 1 | Synthesis Example 1 | — | |
| Comparative Example 2 | — | Synthesis Example 8 | |

Evaluation of Coating Uniformity 2 mL aliquots of the compositions according to Example 1 to 9 and Comparative Example 1 were each respectively cast on an 8-inch wafer, spin-coated with an auto track (ACT-8, TEL (Tokyo Electron Limited)) at 1,500 rpm for 20 seconds, and then cured at 210° C. for 90 seconds to form 250 Å-thick thin films.

In addition, the under layer compositions was additionally diluted, and then spin-coated and cured as aforementioned to form 50 Å-thick ultrathin films.

Coating uniformity was evaluated by measuring a thickness at 51 different points on the horizontal axis, and the results are shown in Table 2. The difference (Å) between a maximum value and a minimum value of the 51 thickness measurements was calculated as a measure of coating uniformity, and herein, the smaller the difference was, the better or more excellent (e.g., uniform in thickness) the coating uniformity was.

TABLE 2

| | Coating uniformity (maximum value-minimum value (Å)) | |
|---|---|---|
| | @ 250 Å film | @ 50 Å film |
| Example 1 | 3.5 | 0.9 |
| Example 2 | 3.5 | 1.2 |
| Example 3 | 3.7 | 1.0 |
| Example 4 | 3.6 | 1.1 |
| Example 5 | 2.6 | 1.4 |
| Example 6 | 3.2 | 0.3 |
| Example 7 | 2.0 | 0.8 |
| Example 8 | 3.5 | 1.1 |
| Example 9 | 3.0 | 0.8 |
| Comparative Example 1 | 15 | 13 |

Referring to Table 2, the resist underlayer compositions according to Examples 1 to 9 exhibited excellent (improved) coating uniformity compared with the resist underlayer composition according to Comparative Example 1.

Evaluation of Film Density

Each resist underlayer composition according to Examples 1 to 9 and Comparative Example 2 was spin-coated on a silicon substrate and then, heat-treated on a hot plate at 210° C. for 90 seconds to form an about 100 nm-thick resist underlayer.

Subsequently, the density of the resist underlayer was measured, and the results are shown in Table 3. The density of the resist underlayer was measured by using an X-ray diffractometer (Model: X'Pert PRO MPD, Malvern Panalytical Ltd., Netherlands).

TABLE 3

| | Film density (g/cm$^3$) |
|---|---|
| Example 1 | 1.39 |
| Example 2 | 1.36 |
| Example 3 | 1.38 |
| Example 4 | 1.38 |
| Example 5 | 1.35 |
| Example 6 | 1.35 |
| Example 7 | 1.34 |
| Example 8 | 1.37 |
| Example 9 | 1.33 |
| Comparative Example 2 | 1.25 |

Referring to Table 3, each of the films formed of the resist underlayer compositions according to Examples 1 to 9 exhibited a high density compared with the film formed of the resist underlayer composition according to Comparative Example 2. Without being bound by the correctness of any explanation or theory, it is thought that the film density was improved by the use of the polymer (or the compound) including the substituted polycyclic aromatic ring group and (e.g., in combination with) the polymer having a high ratio of a core including the hetero cycle structure included in the resist underlayer compositions according to Examples 1 to 9.

Referring to the results of Table 3, resist underlayer compositions according to embodiments of the present disclosure, such as those of Examples 1 to 9, may form films with a denser structure, compared with Comparative Example 2.

Evaluation of Exposure Characteristics

Each of the compositions according to Examples 1 to 9 and Comparative Example 2 were respectively coated in a spin-on coating method, and then heat-treated on a hot plate at 210° C. for 90 seconds to form about 10 nm-thick resist underlayers.

Subsequently, on each of the photoresist underlayers, a photoresist solution was coated in a spin-on coating method, and then heat-treated on a hot plate at 110° C. for 1 minute to form photoresist layers. The photoresist layers were each exposed to light with an acceleration voltage of 100 keV utilizing an e-beam exposer (Elionix Inc.), and then heat-treated at 110° C. for 60 seconds. Subsequently, the photoresist layers were developed with a 2.38 mass % (wt %) aqueous solution of tetramethylammonium hydroxide (TMAH) at 23° C. and rinsed with pure water for 15 seconds to form photoresist patterns of line and space (L/S).

Then, optimum energy of the photoresist patterns was evaluated, and the results are shown in Table 4. Herein, the optimum energy (Eop, µC/cm$^2$) denotes an exposure dose for resolving 100 nm line and space (L/S) photoresist pattern at 1:1, and in Table 4, the Eop's of Examples 1 to 9 are expressed as relative values, compared with the Eop of Comparative Example 2.

TABLE 4

| | Eop (µC/cm$^2$) |
|---|---|
| Example 1 | 0.89 |
| Example 2 | 0.88 |
| Example 3 | 0.84 |
| Example 4 | 0.83 |
| Example 5 | 0.88 |
| Example 6 | 0.89 |
| Example 7 | 0.89 |
| Example 8 | 0.90 |
| Example 9 | 0.91 |
| Comparative Example 2 | 1.0 |

Referring to Table 4, when the photoresist underlayer compositions according to Examples 1 to 9 were each used to form resist underlayers, the photoresist patterns deposited over the photoresist underlayer compositions formed from Examples 1 to 9 exhibited better or excellent optimum energy compared with Comparative Example 2.

Accordingly, referring to the results of Table 4, when the resist underlayer compositions according to embodiments of the present disclosure, such as those of Examples 1 to 9, are used, a photoresist pattern deposited over the photoresist underlayer compositions may have improved sensitivity compared with Comparative Example 2.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Hereinbefore, the certain embodiments of the present disclosure have been described and illustrated, however, it is apparent to a person with ordinary skill in the art that the present disclosure is not limited to the embodiment as described, and may be variously modified and transformed without departing from the spirit and scope of the present disclosure. Accordingly, the modified or transformed embodiments as such may not be understood separately from the technical ideas and aspects of the present disclosure, and the modified embodiments are within the scope of the appended claims and equivalents thereof.

| Description of Some of the Symbols |
|---|
| 100: substrate |
| 102: thin film |
| 104: resist underlayer |
| 106: photoresist layer |
| 108: photoresist pattern |
| 110: mask |
| 112: organic layer pattern |
| 114: thin film pattern |

What is claimed is:

1. A resist underlayer composition, comprising:
(A) a polymer comprising a structural unit represented by Chemical Formula 1, a compound represented by Chemical Formula 2, or a combination thereof;
(B) a polymer comprising a structure in which at least one moiety represented by Chemical Formula 3 or Chemical Formula 4, and a moiety represented by Chemical Formula 7 are bound to each other; and
(C) a solvent:

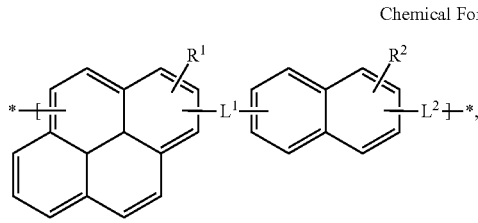

Chemical Formula 1 wherein, in Chemical Formula 1,
R$^1$ and R$^2$ are each independently a hydroxy group, a substituted or unsubstituted C1 to C20 alkoxy group, a halogen, a substituted or unsubstituted C1 to C20 alkyl group, a substituted or unsubstituted C2 to C30 alkenyl group, a substituted or unsubstituted C2 to C20 alkynyl group, a substituted or unsubstituted C6 to C30 aryl group, a substituted or unsubstituted C6 to C30 heteroaryl group, a substituted or unsubstituted vinyl group, or a combination thereof,
L$^1$ and L$^2$ are each independently a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, and

* is a linking point;

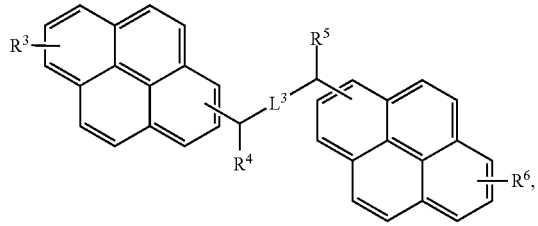

Chemical Formula 2 wherein, in Chemical Formula 2,
R$^3$ to R$^6$ are each independently a hydroxy group, a thiol group, a cyano group, a substituted or unsubstituted amino group, a halogen atom, a substituted or unsubstituted C1 to C30 alkyl group, a substituted or unsubstituted C1 to C30 alkoxy group, a substituted or unsubstituted C6 to C30 aryl group, or a combination thereof, and
L$^3$ is a single bond, a substituted or unsubstituted C1 to C30 alkylene group, a substituted or unsubstituted C6 to C30 arylene group, or a combination thereof;

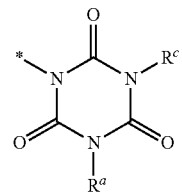

Chemical Formula 3

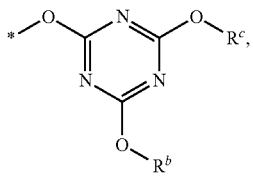

Chemical Formula 4 wherein, in Chemical Formulae 3 and 4,
R$^a$ and R$^b$ are each independently hydrogen, deuterium, a substituted or unsubstituted C1 to C10 alkyl group, a substituted or unsubstituted C2 to C20 alkenyl group, a substituted or unsubstituted C2 to C20 vinyl group, a substituted or unsubstituted C2 to C20 alkynyl group, a substituted or unsubstituted C3 to C20 cycloalkyl group, a substituted or unsubstituted C6 to C20 aryl group, a substituted or unsubstituted C1 to C10 heteroalkyl group, a substituted or unsubstituted C2 to C20 heteroalkenyl group, a substituted or unsubstituted C3 to C20 heterocycloalkyl group, or a substituted or unsubstituted C6 to C20 heteroaryl group, or a combination thereof,
R$^c$ is a terminal group that is a substituted or unsubstituted C1 to C10 alkyl group, a substituted or unsubstituted C2 to C20 alkenyl group, a substituted or unsubstituted C2 to C20 alkynyl group, a substituted or unsubstituted C3 to C20 cycloalkyl group, a substituted or unsubstituted C1 to C10 heteroalkyl group, a substituted or unsubstituted C2 to C20 heteroalkenyl group, a substituted or unsubstituted C3 to C20 heterocycloalkyl group, a structural unit represented by Chemical Formula 5 or Chemical Formula 6, or a combination thereof, and the at least one moiety represented by Chemical Formula 3 or 4 is linked to * in Chemical Formula 7 at each * position;

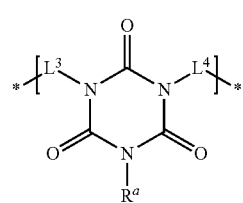

Chemical Formula 5

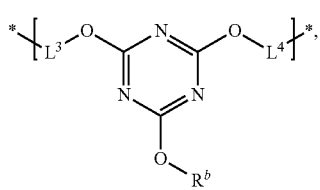

Chemical Formula 6 wherein, in Chemical Formulae 5 and 6, $L^3$ and $L^4$ are each independently a substituted or unsubstituted C1 to C20 alkylene group, a substituted or unsubstituted C1 to C20 heteroalkylene group, or a combination thereof, $R^a$ and $R^b$ are each independently the same as defined in Chemical Formula 3 and Chemical Formula 4, and

* is a linking point; and

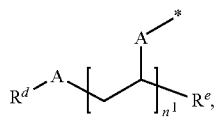

Chemical Formula 7 wherein, in Chemical Formula 7,

A is a single bond, a substituted or unsubstituted C1 to C10 alkylene group, —C(=O)—, —(CO)O—, —O(CO)O—, or a combination thereof, X is a single bond, —O—, —S—, —S(=O)—, —S(=O)$_2$—, —C(=O)—, —(CO)O—, —O(CO)O—, —NR— (wherein R is hydrogen, deuterium, or a C1 to C10 alkyl group), or a combination thereof, $R^d$ is hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, $R^e$ is one of hydrogen, deuterium, or a C1 to C10 alkyl group, $n^1$ is 2 to 10,000, and

* is linked to Chemical Formula 3 or Chemical Formula 4, or linked to hydrogen, deuterium, a halogen, a hydroxy group, a cyano group, a nitro group, an amino group, an epoxy group, a vinyl group, a (meth)acrylate group, an oxetane group, a thiol group, a carboxyl group, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C10 alkoxy group, a substituted or unsubstituted C3 to C10 cycloalkyl group, a substituted or unsubstituted C6 to C30 aryl group, a substituted or unsubstituted C6 to C30 aryloxy group, or a combination thereof, provided that at least one of Chemical Formula 3 or Chemical Formula 4 is linked to * of Chemical Formula 7.

2. The resist underlayer composition of claim 1, wherein:

$R^1$ and $R^2$ of Chemical Formula 1 are each independently a hydroxy group, a substituted or unsubstituted C1 to C20 alkoxy group, a substituted or unsubstituted C1 to C20 alkyl group, a substituted or unsubstituted C6 to C30 aryl group, a substituted or unsubstituted vinyl group, or a combination thereof, $L^1$ and $L^2$ of Chemical Formula 1 are each independently a single bond, a substituted or unsubstituted C1 to C20 alkylene group, a substituted or unsubstituted C3 to C20 cycloalkylene group, a substituted or unsubstituted C6 to C30 arylene group, a substituted or unsubstituted C1 to C20 heteroalkylene group, a substituted or unsubstituted C2 to C20 heterocycloalkylene group, a substituted or unsubstituted C2 to C30 heteroarylene group, or a combination thereof, $R^3$ to $R^6$ of Chemical Formula 2 are each independently a hydroxy group, a thiol group, a cyano group, a substituted or unsubstituted C1 to C30 alkoxy group, or a combination thereof, and $L^3$ of Chemical Formula 2 is a substituted or unsubstituted phenylene group, a substituted or unsubstituted naphthalenylene group, a substituted or unsubstituted biphenylene group, or a combination thereof.

3. The resist underlayer composition of claim 1, wherein:

$R^a$ and $R^b$ of Chemical Formulae 3 and 4 are each independently a substituted or unsubstituted C1 to C10 alkyl group, a substituted or unsubstituted C2 to C20 alkenyl group, a substituted or unsubstituted C3 to C20 cycloalkyl group, a substituted or unsubstituted C1 to C10 heteroalkyl group, a substituted or unsubstituted C2 to C20 heteroalkenyl group, or a substituted or unsubstituted C3 to C20 heterocycloalkyl group, $R^c$ is a terminal group that is a substituted or unsubstituted C1 to C10 alkyl group, a substituted or unsubstituted C3 to C20 cycloalkyl group, a substituted or unsubstituted C1 to C10 heteroalkyl group, a substituted or unsubstituted C3 to C20 heterocycloalkyl group, a structural unit represented by Chemical Formula 5 or Chemical Formula 6, or a combination thereof, in Chemical Formula 7, A is a single bond, a substituted or unsubstituted C1 to C10 alkylene group, or a combination thereof, X is a single bond, —O—, —S—, —S(=O)—, —S(=O)$_2$—, or a combination thereof, $R^d$ is a substituted or unsubstituted C1 to C20 alkyl group, a substituted or unsubstituted C3 to C10 cycloalkyl group, a substituted or unsubstituted C1 to C30 thioalkyl group, or a combination thereof, and $R^e$ is hydrogen, deuterium, a C1 to C10 alkyl group, or a combination thereof.

4. The resist underlayer composition of claim 1, wherein:
R$^1$ and R$^2$ of Chemical Formula 1 are each independently a hydroxy group,
L$^1$ and L$^2$ are each independently a substituted or unsubstituted C1 to C10 alkylene group, a substituted or unsubstituted C6 to C20 arylene group, or a combination thereof,
R$^3$ to R$^6$ of Chemical Formula 2 are each independently a hydroxy group, and
L$^3$ of Chemical Formula 2 is a substituted or unsubstituted phenylene group.

5. The resist underlayer composition of claim 1, wherein:
R$^a$ and R$^b$ of Chemical Formulae 3 and 4 are independently a substituted or unsubstituted C1 to C10 alkyl group, a substituted or unsubstituted C2 to C20 alkenyl group, or a combination thereof,
R$^c$ of Chemical Formulae 3 and 4 is a substituted or unsubstituted C1 to C10 alkyl group, a substituted or unsubstituted C1 to C10 heteroalkyl group, a structural unit represented by Chemical Formula 5 or Chemical Formula 6, or a combination thereof,
in Chemical Formula 7, A is a substituted or unsubstituted C1 to C5 alkylene group,
X is —S—,
R$^d$ is a substituted or unsubstituted C1 to C10 alkyl group, a substituted or unsubstituted C1 to C10 thioalkyl group, or a combination thereof, and
R$^e$ is a C1 to C10 alkyl group.

6. The resist underlayer composition of claim 1, wherein the polymer comprising a structural unit represented by Chemical Formula 1 comprises a structural unit represented by Chemical Formula 1-1, a structural unit represented by Chemical Formula 1-2, or a combination thereof:

Chemical Formula 1-1

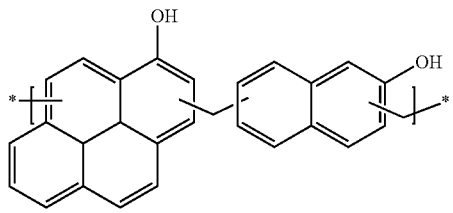

Chemical Formula 1-2

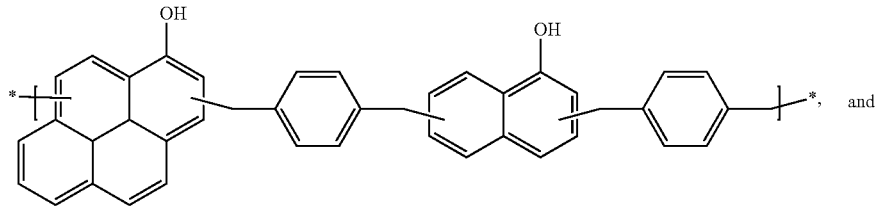

and wherein, in Chemical Formulae 1-1 and 1-2,
* a linking point.

7. The resist underlayer composition of claim 1, wherein the compound represented by Chemical Formula 2 is a compound represented by Chemical Formula 2-1:

Chemical Formula 2-1

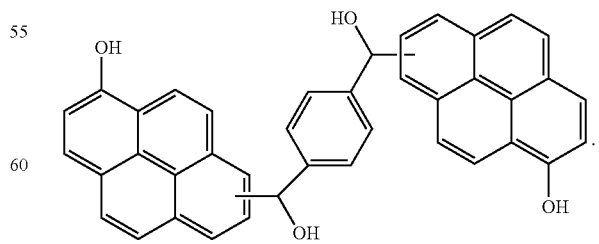

8. The resist underlayer composition of claim 1, wherein the polymer of (B) is represented by any one of Chemical Formulae 3-1 to 3-5 or Chemical Formulae 4-1 to 4-5:

Chemical Formula 3-1
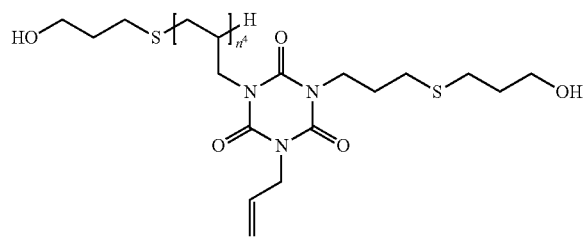
Chemical Formula 3-2
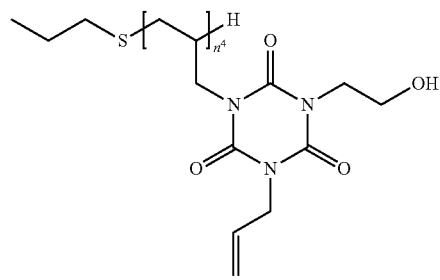
Chemical Formula 3-3
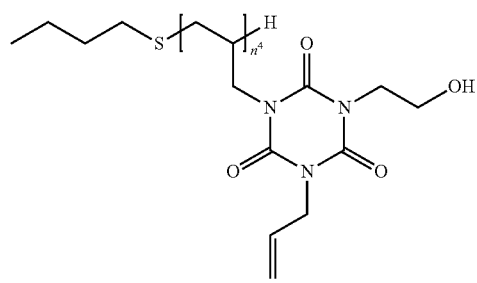
Chemical Formula 3-4
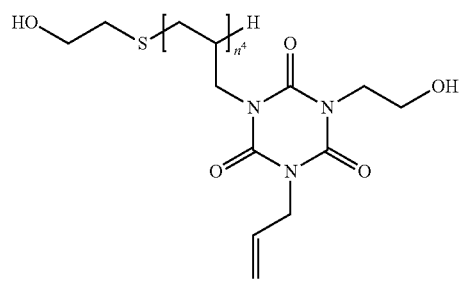
Chemical Formula 3-5
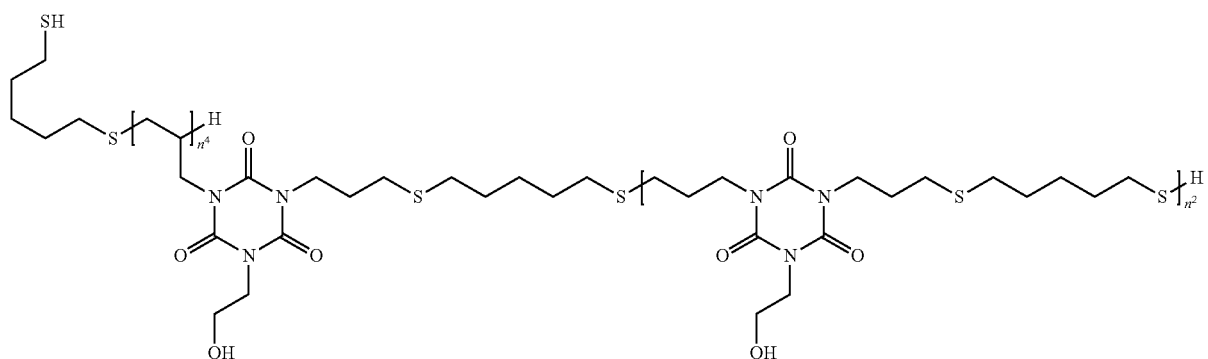
Chemical Formula 4-1
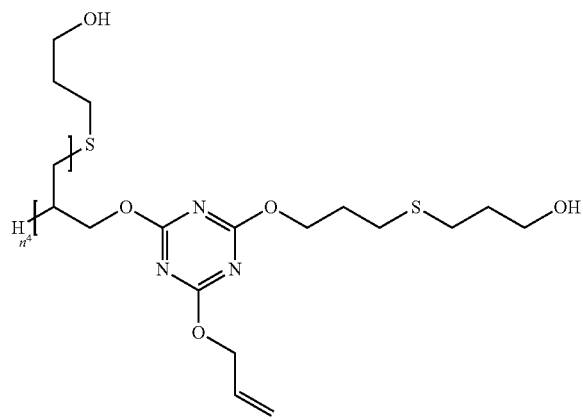
Chemical Formula 4-2
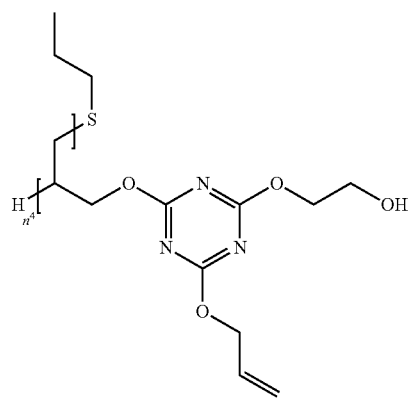

-continued

Chemical Formula 4-3

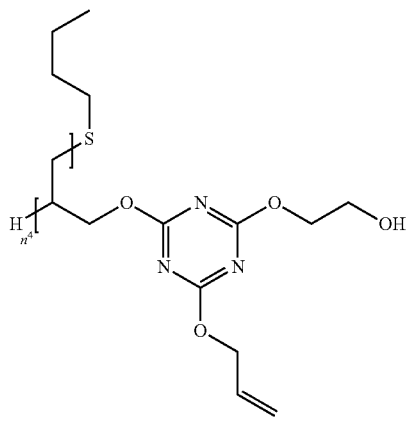

Chemical Formula 4-4

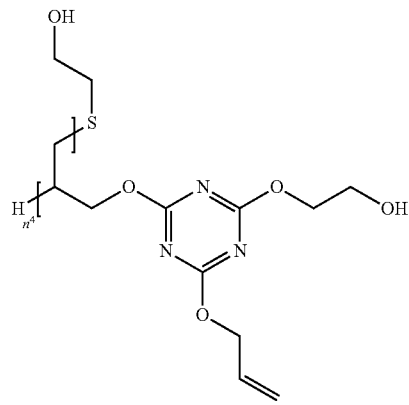

Chemical Formula 4-5

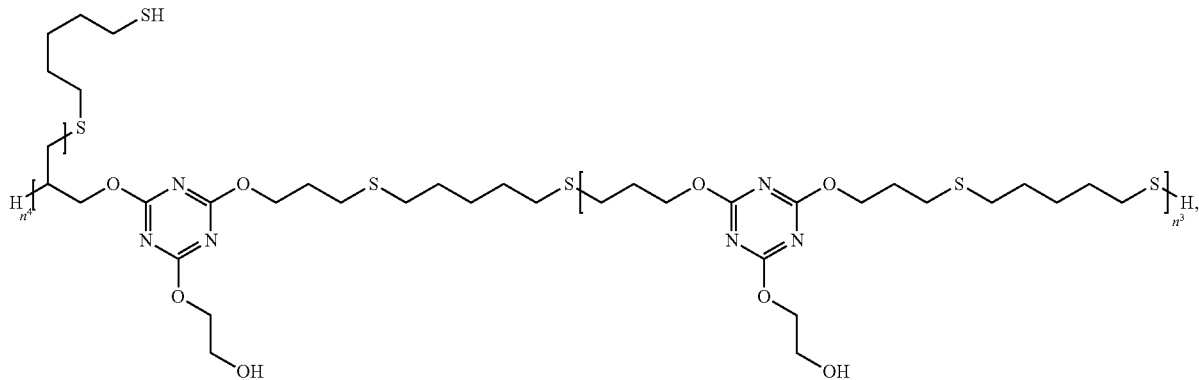

and
wherein, in Chemical Formulae 3-1 to 3-5 and Chemical Formulae 4-1 to 4-5, $n^4$ is 2 to 10,000,
in Chemical Formula 3-5, $n^2$ is 1 to 10,000, and
in Chemical Formula 4-5, $n^3$ is 1 to 10,000.

9. The resist underlayer composition of claim 1, wherein (A) and (B) are comprised in a weight ratio of about 80:20 to about 20:80.

10. The resist underlayer composition of claim 1, wherein a weight average molecular weight of the polymer comprising a structural unit represented by Chemical Formula 1 is about 1,000 g/mol to about 10,000 g/mol.

11. The resist underlayer composition of claim 1, wherein a weight average molecular weight of (B) is about 2,000 g/mol to about 100,000 g/mol.

12. The resist underlayer composition of claim 1, wherein a sum weight of (A) and (B) is about 0.01 wt % to about 5 wt % based on a total weight of the resist underlayer composition.

13. The resist underlayer composition of claim 1, further comprising at least one polymer selected from an acrylic resin, an epoxy resin, a novolac resin, a glycoluril resin, and a melamine resin.

14. The resist underlayer composition of claim 1, further comprising an additive comprising a surfactant, a thermal acid generator, a plasticizer, or a combination thereof.

15. A method of forming a pattern, the method comprising:
forming an etching target layer on a substrate,
forming a resist underlayer by applying the resist underlayer composition of claim 1 on the etching target layer,
forming a photoresist pattern on the resist underlayer, and
sequentially etching the resist underlayer and the etching target layer utilizing the photoresist pattern as an etching mask.

16. The method of claim 15, wherein the forming of the photoresist pattern comprises:
forming a photoresist layer on the resist underlayer,
exposing the photoresist layer, and
developing the photoresist layer.

17. The method of claim 15, wherein the forming of the resist underlayer further comprises:
coating the resist underlayer composition, and
heat treating the resist underlayer at a temperature of about 100° C. to about 500° C.

* * * * *